(12) United States Patent
Wixey et al.

(10) Patent No.: US 7,625,387 B2
(45) Date of Patent: Dec. 1, 2009

(54) SUTURE SECURING DEVICE AND METHOD

(75) Inventors: Matthew A. Wixey, Dana Point, CA (US); Charles C. Hart, Summerville, SC (US); Payam Adlparvar, Lake Forest, CA (US)

(73) Assignee: Applied Medical Resources Corporation, Rancho Santa Margarita, CA (US)

( * ) Notice: Subject to any disclaimer, the term of this patent is extended or adjusted under 35 U.S.C. 154(b) by 650 days.

(21) Appl. No.: 10/702,871

(22) Filed: Nov. 5, 2003

(65) Prior Publication Data

US 2005/0096699 A1 May 5, 2005

(51) Int. Cl.
*A61B 17/04* (2006.01)
(52) U.S. Cl. ...................................... 606/148; 606/151
(58) Field of Classification Search ................. 606/148, 606/232, 60, 72–74, 143, 151; 24/136 L, 24/115 G, 115 R–115 N
See application file for complete search history.

(56) References Cited

U.S. PATENT DOCUMENTS

| | | | |
|---|---|---|---|
| 2,379,676 A | | 7/1945 | Blackstone |
| D209,171 S | * | 11/1967 | Myatt ........................... D8/394 |
| 3,407,454 A | | 10/1968 | Myatt |
| 4,724,584 A | * | 2/1988 | Kasai ....................... 24/115 G |
| 5,078,731 A | | 1/1992 | Hayhurst |
| 5,197,166 A | * | 3/1993 | Meier et al. ................ 24/115 G |
| 5,258,015 A | | 11/1993 | Li |
| 5,282,811 A | | 2/1994 | Booker |
| 5,282,832 A | * | 2/1994 | Toso et al. ................... 606/232 |
| 5,383,905 A | | 1/1995 | Golds |
| 5,409,499 A | | 4/1995 | Yi |
| 5,514,159 A | | 5/1996 | Matula |
| 5,531,763 A | | 7/1996 | Mastri et al. |
| 5,584,835 A | * | 12/1996 | Greenfield ................... 606/73 |
| 5,645,553 A | | 7/1997 | Kolesa et al. |
| 5,666,699 A | | 9/1997 | Takahashi |

(Continued)

OTHER PUBLICATIONS

International Search Authority, International Search Report and Written Opinion for PCT /US04/35420, mailed Feb. 24, 2006.

(Continued)

*Primary Examiner*—Julian W Woo
*Assistant Examiner*—Melissa Ryckman
(74) *Attorney, Agent, or Firm*—John F. Heal; David G. Majdali; Patrick Y. Ikehara

(57) ABSTRACT

The invention is directed to a device and method for securing a passed surgical suture in a manner similar to a tied knot. The suture securing device comprises a male piece having a top portion, a center shaft having one end connected to the top portion, and an end member having a capturing feature connected to another end of the center shaft; and a female piece having a top end and a bottom end comprising a column being generally cylindrical in shape and forming a hollow opening along its length, wherein the opening slidingly receives the center shaft and a suture to be captured and held by the capturing feature, the suture being secured in place between the column and the center shaft. The assembled male and female pieces are irreversibly interlocked and form a lightly compressed, convoluted or tortuous pathway. The capturing feature is formed to engage and obliquely capture the suture from different angles.

41 Claims, 20 Drawing Sheets

U.S. PATENT DOCUMENTS

| | | | |
|---|---|---|---|
| 5,681,351 A | 10/1997 | Jamiolkowski | |
| 5,940,942 A | 8/1999 | Fong | |
| 5,964,769 A | 10/1999 | Wagner | |
| 5,972,009 A | 10/1999 | Fortier | |
| 6,086,608 A | 7/2000 | Ek | |
| 6,125,574 A | 10/2000 | Ganaja | |
| 6,126,677 A * | 10/2000 | Ganaja et al. | 606/232 |
| 6,306,159 B1 | 10/2001 | Schwartz | |
| 6,391,030 B1 | 5/2002 | Wagner | |
| 6,449,810 B1 | 9/2002 | Kuwayama | |
| 6,468,293 B2 | 10/2002 | Bonutti | |
| 6,524,328 B2 * | 2/2003 | Levinson | 606/232 |
| 7,033,379 B2 * | 4/2006 | Peterson | 606/232 |
| 7,033,380 B2 * | 4/2006 | Schwartz et al. | 606/232 |

OTHER PUBLICATIONS

Co-Pending U.S. Appl. No. 11/954,457, filed Dec. 12, 2007; Title: Surgical Clip.

Co-Pending U.S. Appl. No. 10/935,967, filed Sep. 8,2004; Title: Surgical Clip.

Co-Pending U.S. Appl. No. 10/612,631, filed Jul. 2, 2003; Title: Interlocking Suture Clinch.

Co-Pending U.S. Appl. No. 10/533,398, filed Apr. 30, 2005; Title: Surgical Staple-Clip and Applier.

Co-Pending U.S. Appl. No. 11/280,098, filed Nov. 15, 2005; Title: Partial Occlusion Surgical Guide Clip.

Co-Pending U.S. Appl. No. 10/543,800, filed Jul. 29, 2005; Title: Spring Clip and Method for Assembling Same.

Co-Pending U.S. Appl. No. 10/986,993, filed Nov. 12, 2004; Title: Overmolded Grasper Jaw.

Co-Pending U.S. Appl. No. 10/817,259, filed Apr. 2, 2004; Title: Suture Clip With Stop Ribs and Method for Making Same.

* cited by examiner

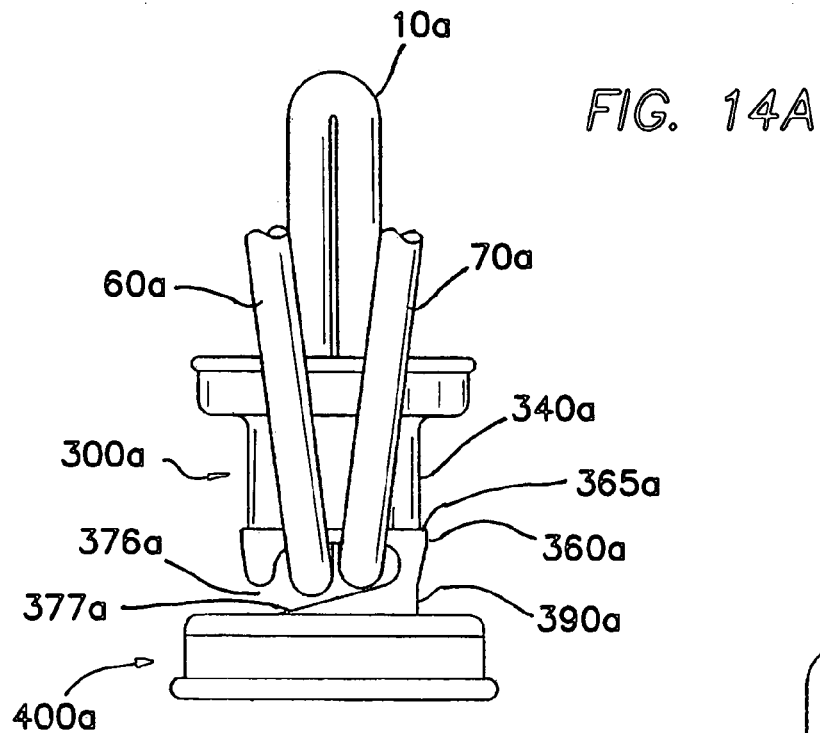
FIG. 14A
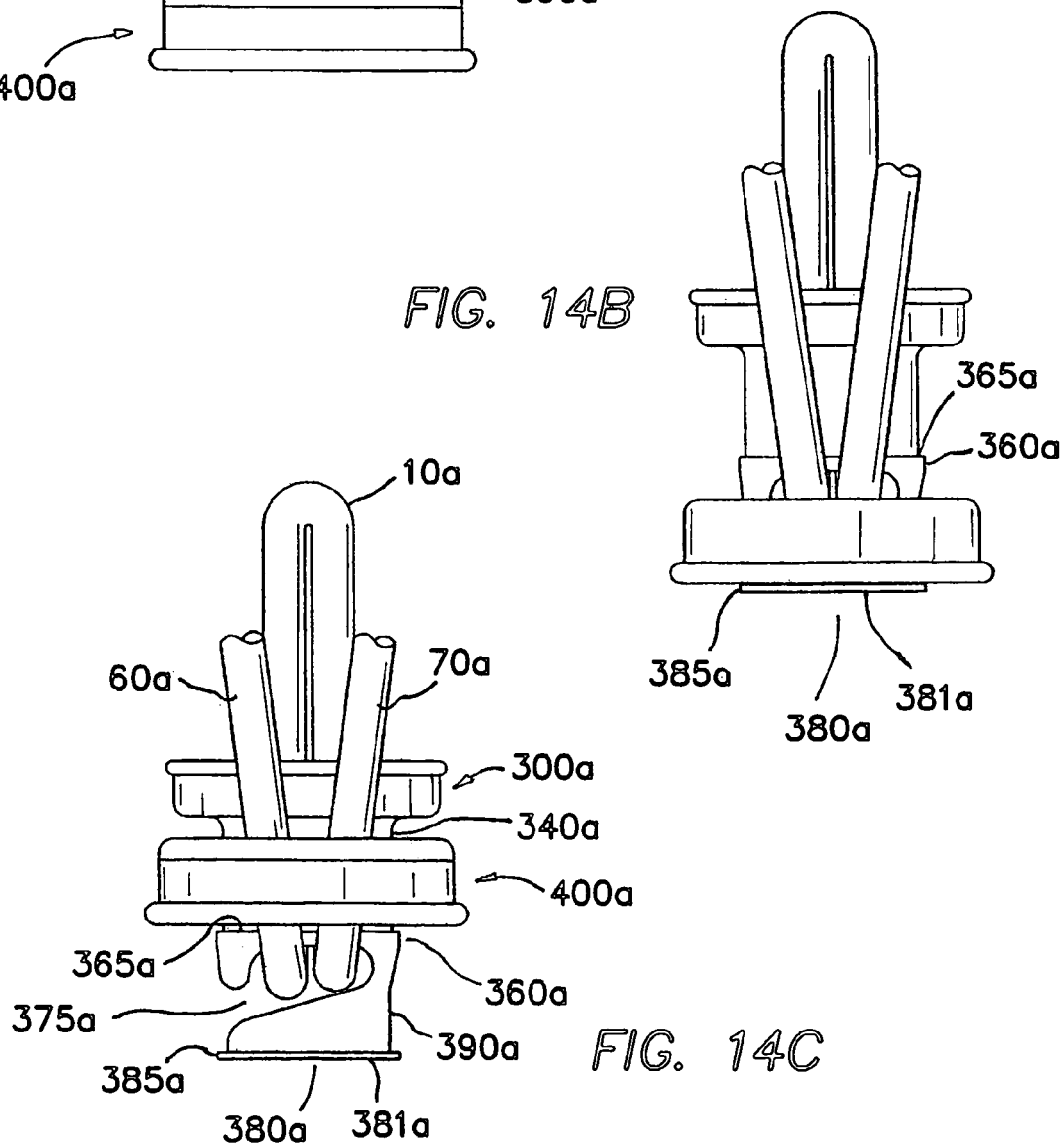
FIG. 14B
FIG. 14C

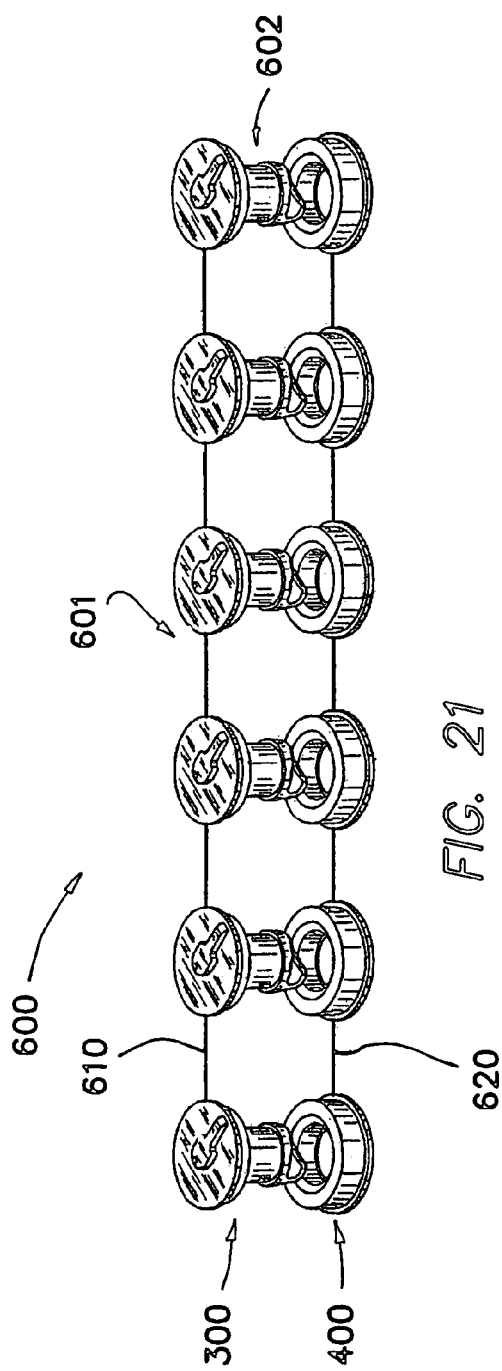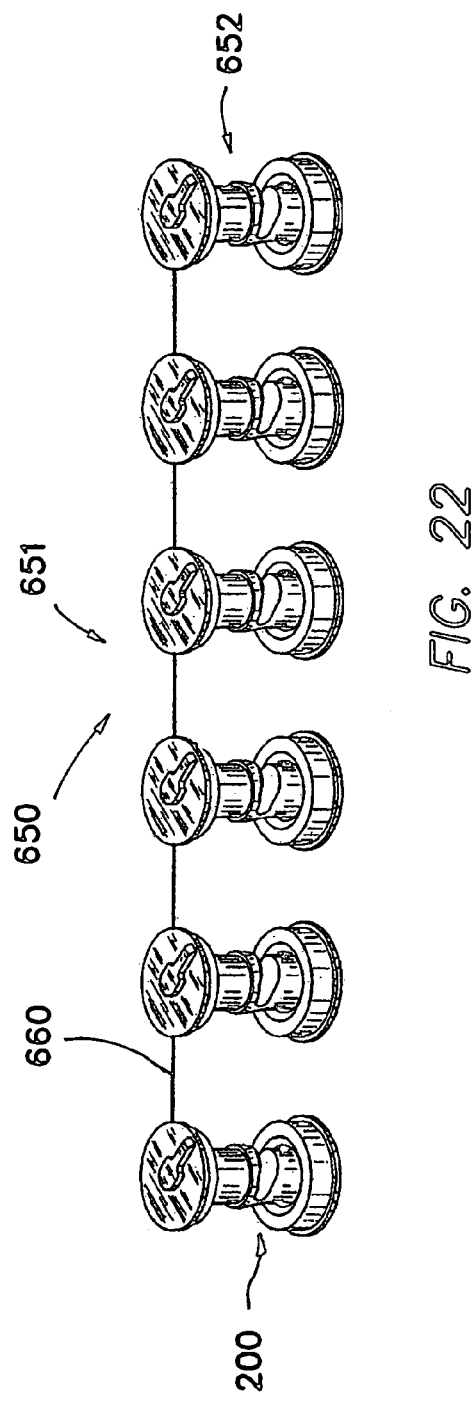

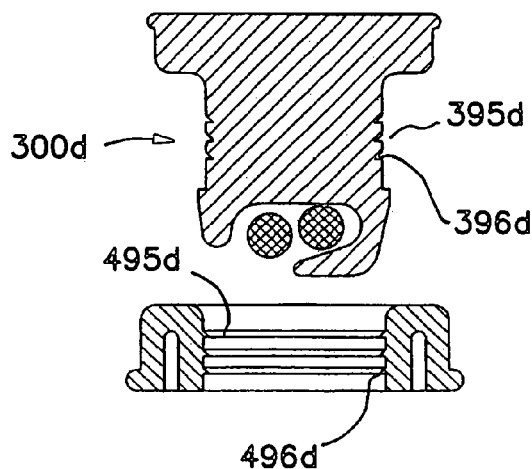
FIG. 25A
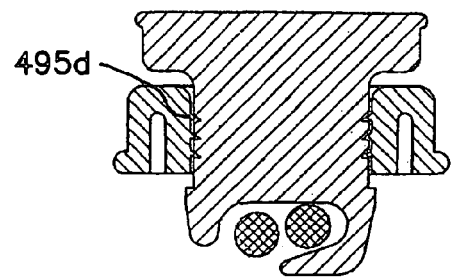
FIG. 25B
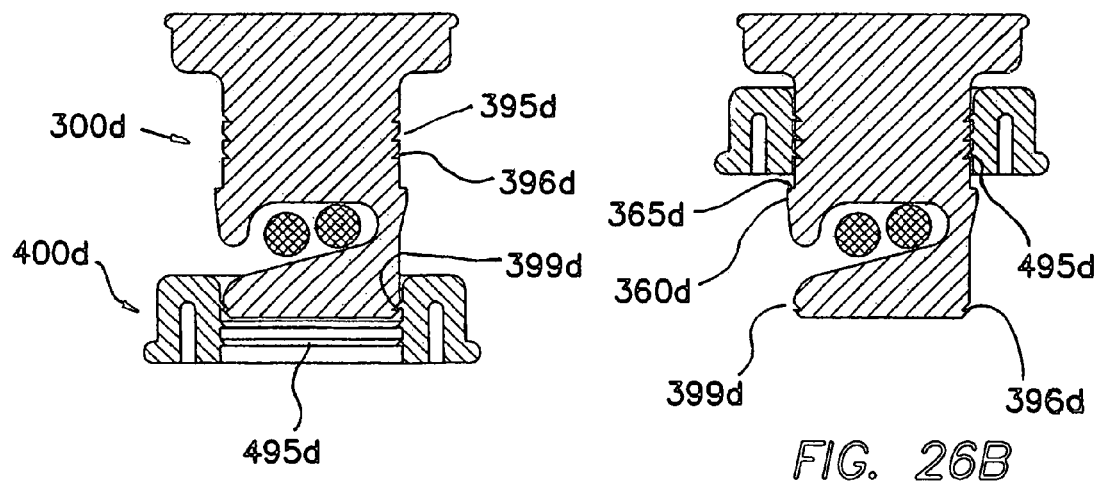
FIG. 26A
FIG. 26B

SUTURE SECURING DEVICE AND METHOD

BACKGROUND OF THE INVENTION

1. Field of the Invention

This invention generally relates to surgical clips and clamps and, in particular, to an interlocking device and method for securing suture ends when a suture is placed.

2. Discussion of the Relevant Art

When a wound is created in body tissue, either intentionally in the case of an incision, or unintentionally in case of an accident, it is desirable to close the site by engaging tissue portions on either side of the separation and drawing those portions into close proximity. Over time, tissues in close proximity will form a scar closing the wound.

Wound-closure systems of the past have included adhesives and clamps. However, the most common closure devices typically involve sutures which can be threaded through the opposing tissue portions and pulled tight to close the wound. In order to hold the suture taught over an extended period of time, a knot is commonly formed in the suture ends. Most surgeons would agree that suturing is an art form learned over an extended period of time. There are many types of sutures and knots, each providing certain advantages in a particular operative setting. At least as complicated as the suturing itself is the knot-tying which must occur to secure each of the sutures. Where individual sutures are placed to close a long wound, an individual knot must be tied in each place.

Knots differ considerably in their configuration, function, complexity, and characteristics. By way of example, it will be noted that knots typically involve several throws of the suture ends relative to each other. In one common knot, three half-hitches are used with the first half-hitch having four throws and each subsequent half-hitch having three throws. In this case, the tying of a single knot to close a single suture involves about ten throws. The simpler knots may be easier to tie, but in distant locations even the simple knots can be complicated where it is difficult to achieve proximity to the suture site. In these locations, more complicated slip knots have been used. These knots can be tied at a remote location and then slipped down to the surgical site. Except for a few extremely complex knots, such as the Tayside or Roeder knots, slip knots have the undesirable tendency to slip in both directions. As a result, their ease of tying and movement to the surgical site is offset by their tendency to lose their grip at the suture site.

From these few examples it can be appreciated that knots, as a suture-closing system, are time-consuming, difficult to tie, hard to place, often unreliable as a holding system, difficult to adjust and impossible to relocate. Especially in the context of a laparoscopic procedure, it is noteworthy that the surgeon may lose the tactile feedback associated with tension on the suture as the knot is being tied due to the remote nature of the laparoscopic modality. Accordingly, there is a need in the art for an improved suture securing system whereby a suture may be placed under tension without threading.

SUMMARY OF THE INVENTION

The present invention includes a suturing system which overcomes the disadvantages associated with suture knots, clamps, and adhesive. In particular, the present invention is directed to a device and method for securing a passed surgical suture in a manner similar to a tied knot but with greater efficiency. In one aspect of the invention, the suture securing device comprises a male piece having a top portion, a center shaft having one end connected to the top portion, and an end member having a capturing feature connected to another end of the center shaft; and a female piece having a top end and a bottom end comprising a column being generally cylindrical in shape and forming a hollow opening along its length, wherein the opening slidingly receives the center shaft and a suture to be captured and held by the capturing feature, the suture being secured in place between the column and the center shaft. The assembled male and female pieces are irreversibly interlocked and form a lightly compressed, convoluted or tortuous pathway. The capturing feature is formed to engage and obliquely capture the suture from different angles. The top portion may further comprise a flat portion and an alignment feature for aligning the male piece in an applier. The end member of the male piece may further comprise a ledge for mating with an undercut in a distal portion of the female piece when the male and female pieces are fully engaged and compressed. The center shaft may have a reduced diameter section to allow the suture to be placed between the column and the center shaft without damaging the suture. The female piece may further comprise a flange at a distal end for aligning the female piece in an applier. The radii of the male and female pieces are preferably greater than the radius of the suture.

The capturing feature may further comprise a retention portion to retain the male piece within the female piece in a pre-compressed condition. The retention portion further comprises an enlargement that engages an undercut within the opening of the female piece. The enlargement may include teeth, pins or cogs. The female piece may further comprise a ring-shaped compression relief that allows bi-directional movement of the male piece within the opening of the female piece.

The securing device may further comprise a link formed between the male piece and the female piece to retain the male piece and the female piece in a desired position and orientation for introduction into an applier and to maintain a desired arrangement for capturing the suture. The link may be a tether formed when the male and female pieces are formed. The link may be attached to the top portion of the male piece and the bottom end of the female piece. The link may also be attached to the capturing feature and the top end of the female piece. The link may be severed and removed after placement and assembling of the male and female pieces. The link is formed of a deformable material to provide flexibility in one plane while maintaining alignment in an opposite plane.

In another aspect of the invention, a suture securing device is disclosed comprising a first interlocking member having a substantially spherical shape, a proximal portion having a first diameter, a mid-portion having a second diameter, and a distal portion having a third diameter and a slot for securing a suture; and a ring-shaped second interlocking member having an opening for fitting into the mid-portion of the first interlocking member, wherein the first interlocking member is formed of an elastomeric material and the second interlocking member is formed of a rigid material, and wherein the second diameter is less than the first diameter and the third diameter. In this aspect of the invention, the suture is secured in place in the slot of the distal portion and between the first and the second interlocking members. The third diameter may be less than the first diameter to facilitate placement of the second interlocking member into the first interlocking member.

In another aspect of the invention, a method for applying a suture securing device is disclosed comprising the steps of: (1) providing the suture securing device comprising a male piece having a top portion, a center shaft having one end connected to the top portion, and an end member having a capturing feature connected to another end of the center shaft; and a female piece having a top end and a bottom end comprising a column being generally cylindrical in shape and forming a hollow opening along its length, wherein the opening slidingly receives the center shaft and a suture to be captured and held by the capturing feature, the suture being secured in place between the column and the center shaft; (2) aligning the male piece and the female piece at a desired location for applying the suture securing device; and (3) pressing the center shaft of the male piece into the opening of the female piece. The method may further comprise the step of applying a compressive load on the male piece to dislodge an enlargement from an undercut of the female piece and to place the male piece and the female piece in a condition where they may be advanced to a desired position along the suture.

In yet another aspect of the invention, an applier for use with a suture securing device is disclosed comprising an elongate body having a proximal end and a distal end for holding a plurality of suture securing devices, each of the suture securing devices including a male piece and a female piece; a plurality of jaws operatively connected to the distal end of the elongate body such that the male piece is placed within one of the jaws and the female piece is placed within the other jaw; and a handle including elements operatively connected to the proximal end of the body to actuate elements at the distal end of the body, wherein the male piece includes a top portion and a center shaft connected to the top portion, wherein the female piece has a top end and a bottom end comprising a column being generally cylindrical in shape and forming a hollow opening along its length, and wherein the opening slidingly receives the center shaft and a suture that is secured in place between the column and the center shaft. With this aspect of the invention, at least one of the jaws is movable to actuation from the actuation elements associated with the handle. The jaws may include release openings at distal ends or side portions of the jaws. The jaws may be straight, in-line or angled from an axis of the body. The body may further comprise a hinge at the distal end to open and close the jaws. Each of the jaws may include discreet, individual hinged elements cooperating with actuation elements associated with the handle. Each of the suture securing devices may be manually or automatically dispensed by actuating the handle. The applier may further include a cartridge for holding the suture securing devices in an arrangement for advancement to the jaws, and the suture securing devices may be interconnected for easy advancement in the body.

These and other features and advantages of the invention will become more apparent with a discussion of preferred embodiments in reference to the associated drawings.

DESCRIPTION OF THE DRAWINGS

FIGS. 14A-14C illustrate frontal, series views of a pre-assembled interlocking suture clinch as it is progressively closed over strands of suture;

FIG. 21 illustrates a plurality of suture clinches in a manufactured module in one embodiment of the invention;

FIG. 22 illustrates a plurality of suture clinches in a manufactured module in another embodiment of the invention;

FIGS. 25A and 25B are side-section views of another suture clinch further comprising an adjustable interlock;

FIGS. 26A and 26B are side-section views of another suture clinch further comprising an adjustable interlock;

DESCRIPTION OF PREFERRED EMBODIMENT AND BEST MODE OF THE INVENTION

The following is a list of unique terms used in the description of the invention:

CLINCH—a device or component for securing a looped strand or strands of suture material in a manner resembling a tied knot in a tortuous pathway within and between tractive surfaces or faces.

TIED KNOT—a conventional surgical knot comprising multiple throws or combinations of simple tied knots.

THROW—a simple intertwining of strands forming a basic knot such as a "Granny Knot" or a "Square Knot". Several basic or simple knots or throws are combined to form a complex knot.

PASSED SUTURE—a length of suture that has been passed through tissue in combination with an attached needle for the purpose of approximating, holding, repairing or securing tissue.

FREE ENDS—ends of a length of suture that extend before and after the suture has passed through a portion of the tissue.

TORTUOUS PATHWAY—a pathway through or between elements of a device that restricts motion or movement of suture that extends through the pathway.

CROSS-PULL—the two directions in which two strands of a suture may be pulled upon that are at an angle to the axis of the suture that has been passed.

RADIUS POSTULATE—the radius of the suture itself. In the context of suture securement, this represents the minimum radius over which the suture material must conform. A preferred radius is greater than the radius of the suture itself.

LAPAROSCOPIC—surgery that is performed through access ports, such as trocar cannulas. Such procedures require that instruments are operable through access ports. Visualization of the procedure typically requires a small, inserted camera and an external viewing component such as a video monitor.

CLOSED SURGERY—a method of surgery where the internal portion of a subject is isolated from the external portion by access ports.

OPEN SURGERY—surgery where a body wall is surgically opened with an incision to provide surgical access.

INTERRUPTED SUTURE—suturing where each loop of passed suture, or stitch, is tied with a separate knot.

RUNNING SUTURE—suturing where several loops of passed suture, or stitches, are placed and tied with a knot.

INTERRUPTED RUNNING SUTURE—combination of running suture and interrupted suture where each pass of a running suture may be secured in a single pass or stitch.

RADIUS ENCOUNTER—an area or point where one strand of suture crosses another to form a knot.

NOTCHING—damage that occurs to suture when it is compressed or when it is bent over a sharp radius causing a defect in the material and creating a weakness at that point.

Figure 1A:
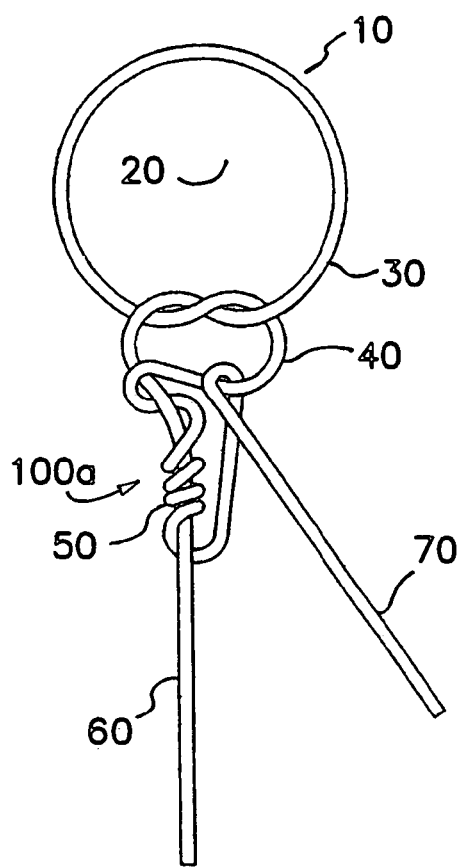
FIG. 1(A) illustrates a complex slip-knot that is commonly used in laparoscopic surgery.
Figure 1B:
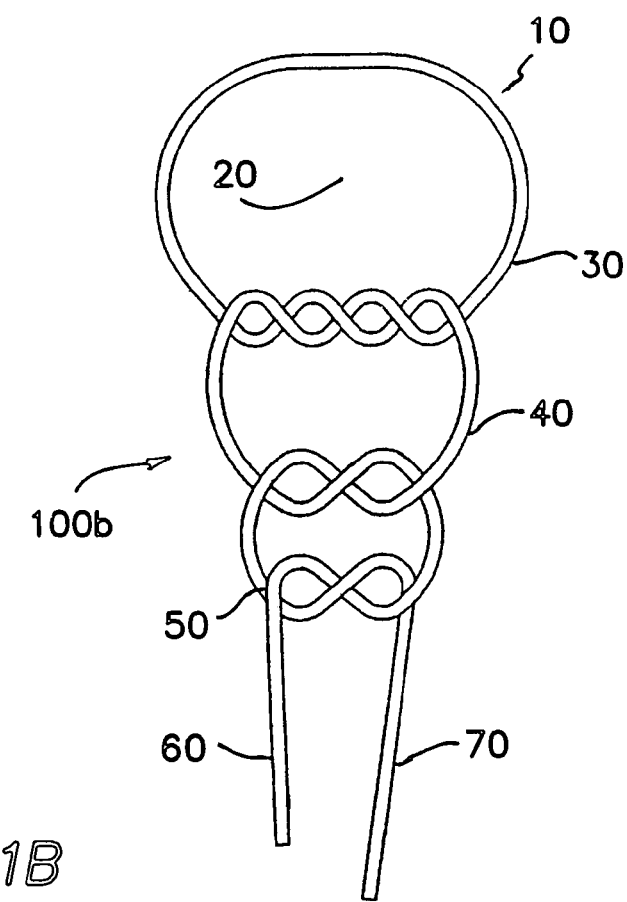
FIG. 1(B) illustrates a multi-throw knot used in both open and laparoscopic surgery.

FIGS. 1(A) and 1(B) illustrate a complex slip-knot 100*a* and a multi-throw surgical knot 100*b*, respectively. Each of these knots 100*a*, 100*b* has an engaging portion 10 and two extending portions 60, 70. The first extending portion 60 is normally associated with a penetrating member such as a needle. The second extending portion 70 normally trails the first extending portion 60 and is reserved for use in securing the engaging portion 10.

It can be readily seen that the stresses placed upon the tied knot 100*a* and 100*b* are seldom along the axis of the engaging portion 10. The stresses are most likely to accumulate across the suture axis. This is commonly referred to as "cross-pull". Therefore, it can generally be stated that the radius over which the suture is required to bend is the radius of the suture. This relationship will be referred to as the radius postulate. The radius encountered in a tied knot is variable as the suture is placed under tension as is the case when a tied knot is tightened securely. The suture material is compressed and this compression results in a smaller radius as material flows away from applied stresses or is stretched. It follows that the smaller the radius over which the suture must pass, the more likely it is that the suture will break at the radius encounter.

In a preferred embodiment, the radius postulate says that the radius over which any given suture passes shall be no less than the radius of the suture itself. Extrapolating this principle provides that a larger radius adds an element of security to the securement of the extending portions of a suture. Most of the knots used in laparoscopic procedures are slip-knots 100*a* that are tied at a first location, sometimes outside of the body cavity (extracorporeal), and subsequently advanced to the desired, second location. The suture is often damaged during the advancing of the tied knot 100*a* along the extending portions 60, 70 of the suture sometimes resulting in breakage. In the case of a tied knot 100*a* and 100*b*, the stress, friction and elongation combine to make tied knots 100*a*, 100*b* the weakest point in the surgical suture loop 20. Therefore, a surgeon may often be required to use a second choice of suture material or suture size simply because his or her first choice may not withstand the knot tying process.

Figure 2:
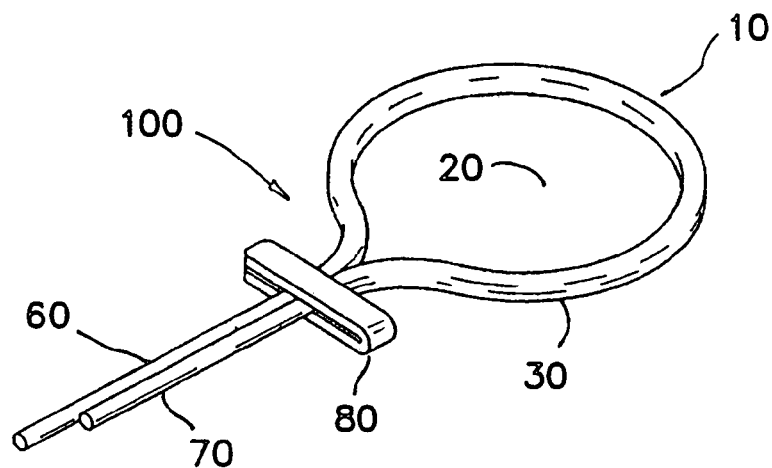
FIG. 2 illustrates a surgical clip used to secure a length of placed suture and to replace a tied knot.
Figure 3:
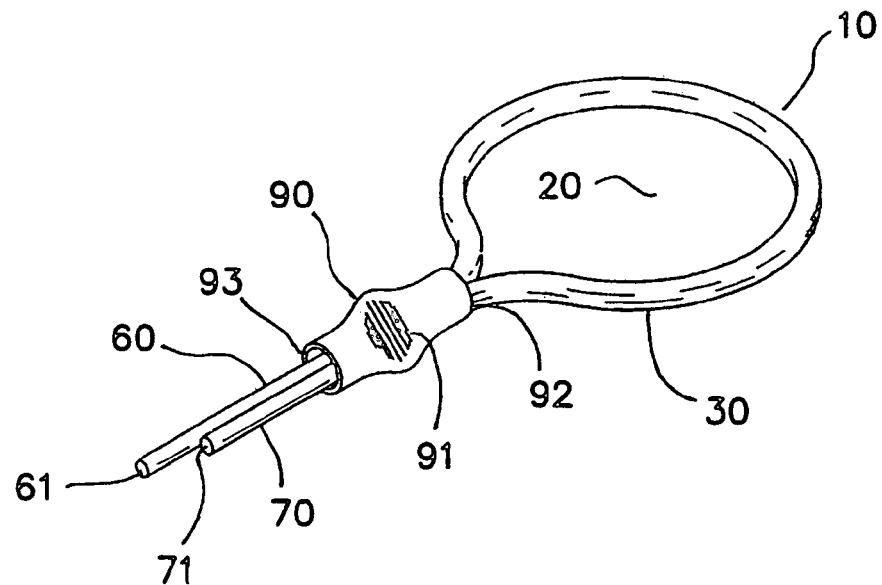
FIG. 3 illustrates a device according to prior art where a hollow tube is placed over extensions of a placed suture to replace a tied knot.

Referring to FIG. 2 and FIG. 3, alternatives to tied surgical knots are shown comprising compressive devices 80, 90 that are placed upon suture extensions 60, 70. In particular, a surgical clip 80 is placed over suture extensions 60, 70 that extend from a loop 10 of suture placed through tissue as illustrated in FIG. 2. The clip 80, usually made of a malleable metal, such as titanium, is compressed over the suture extensions 60, 70. There are several disadvantages to securing suture with clip 80. The suture extensions 60, 70 must be over-compressed to assure that clip 80 does not move along the axis of suture extensions 60, 70 or to prevent slip-off. One must remember that suture is very delicate and very susceptible to notching. Moreover, clip 80 placed upon two suture extensions 60, 70 does not provide stability in the likely event of cross-pull. The suture may migrate and suffer damage due to abrasion.

An alternative to tying knots or securing the suture extensions with a clip is illustrated in FIG. 3 where a hollow tube 90 is placed over suture extensions 60, 70 and subsequently advanced to a preferred location and then compressed and/or bent to secure the suture extensions 60, 70. However, the suture must still be over-compressed. Hollow tube 90 securement relies on friction along the compressed portion 91 of the hollow tube 90 to secure the suture extensions 60, 70. In addition, the cross-pull, although not challenging to the tubular structure 90, requires the suture to bend across the wall of the tube. This requires that a flare or radius be developed at the ends 92, 93 of the tube 90. The most obvious disadvantage is that the tube 90 must be installed over the ends 61, 71 of the suture extensions 60, 70, an action that may require the surgeon to relinquish a preferred position or tension upon the suture extensions 60, 70.

FIGS. 4-10 illustrate the first embodiment of an interlocking suture clinch 200 of the present invention comprising a two-piece interlocking combination of a first interlocking element 300 and a second interlocking element 400. The interlocking suture clinch 200 is formed by pressing the first interlocking member 300 into the second interlocking member 400 to a point where the interlocking members 300, 400 are substantially irreversibly interlocked. In a preferred embodiment of the use of the interlocking suture clinch 200, a pair of suture extensions 60, 70 is forced into a lightly compressed, convoluted or tortuous pathway 250, 255 through the assembled first and second interlocking elements 300, 400. Specifically referring to FIG. 5, the suture 60, 70 is guided into a capturing feature 375 associated with the distal end 370 of the first interlocking element 300. The capturing feature 375 is sized and configured to hold at least a length of suture 60, 70 in a preferred location and position so that it may be subsequently drawn through an opening 450 associated with the second interlocking element 400. The capturing feature 375 is arranged so that it can engage suture extensions 60, 70 obliquely from many angles. In use, a user may approach suture extensions 60, 70 from the side and subsequently engage the suture with the first interlocking suture clinch element 300 then advance the interlocking suture clinch 200 to the preferred location and, finally, compress the interlocking elements 300, 400 to fully secure the suture extensions 60, 70.

As illustrated in FIGS. 4-10 and further described below, the first embodiment of the interlocking suture clinch 200 comprises the first interlocking element 300 and the second interlocking element 400 sized and configured to interlock securely. The first interlocking element 300 further comprises a generally cylindrical body 350 having a proximal end 305 and a distal end 370 and an extending mid-portion 340. The proximal end 305 may comprise an enlarged, flat portion 315 resembling a cap. The enlarged, flat face 310 of the proximal portion 315 may be associated with an alignment feature 311 sized and configured to hold the first interlocking element 300 in a preferred position in an applier. A generous radius 320 is associated with a distal facing portion 321 of the proximal enlargement 315 that complies with a radius postulate that requires all radii be greater than the radius of any suture over which it is forced to bend. As discussed, the distal end 370 of the first interlocking element 300 comprises capturing feature 375 that is sized and configured to receive and hold suture extensions 60, 70.

Capturing feature 375 is supplied with generous radii 376 to comply with the radius postulate. A ledge 365 is associated with distal portion 360 of the cylindrical body 350 that is sized and configured to mate with an associated undercut 460 in a distal portion 405 of the second interlocking element 400 when the two elements 300, 400 are fully engaged and compressed. The extending mid-portion 340 of the cylindrical body 350 further comprises a reduced diameter section that is sized and configured to allow suture extensions 60, 70 to exist between the two interlocking elements 300, 400 without damage to the suture 60, 70.

Figure 5:
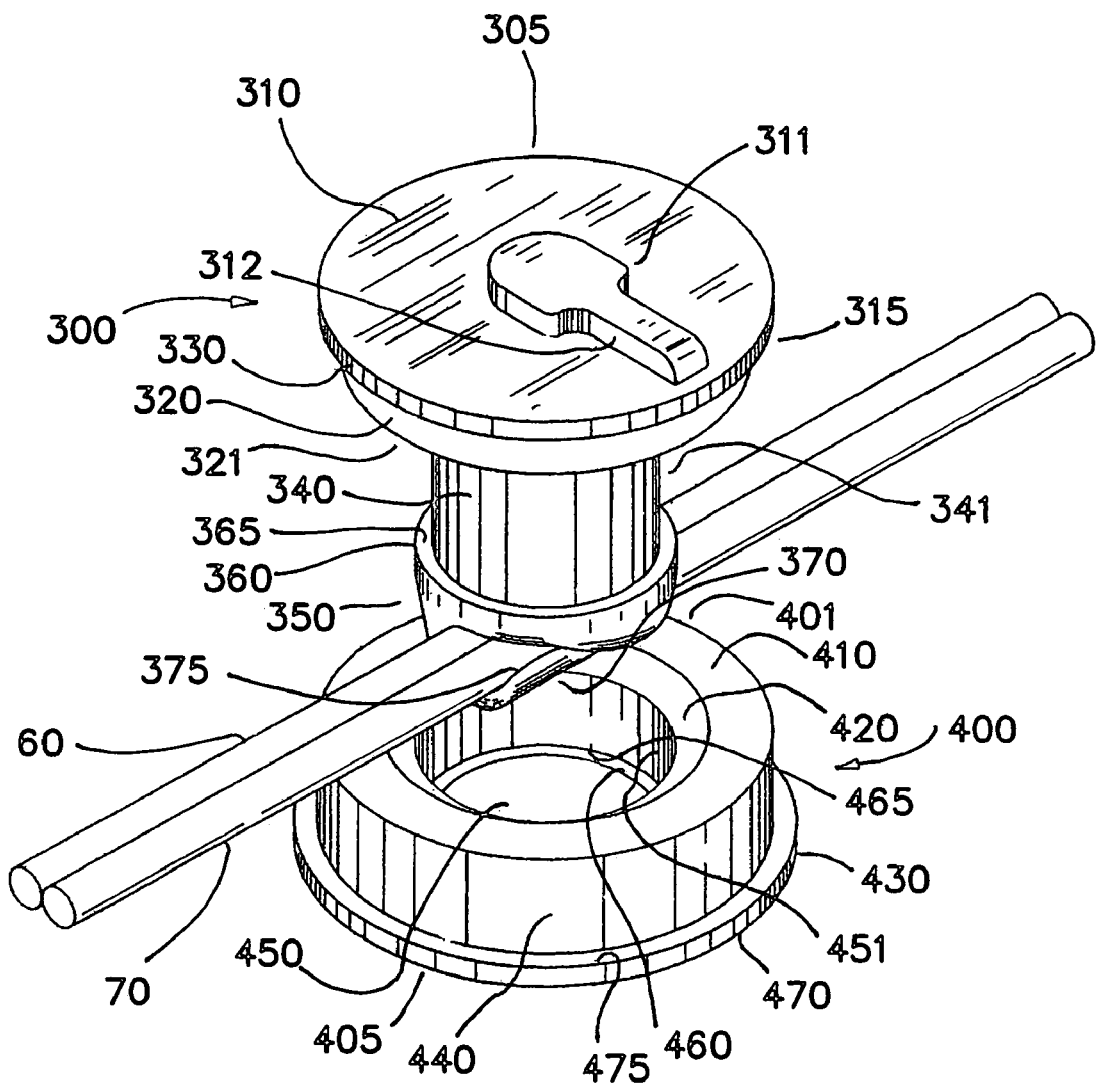
FIG. 5 is a perspective view of an interlocking suture clinch in accordance with another embodiment of the invention where the interlocking elements are positioned prior to being locked together to secure suture strands.
Figure 6:
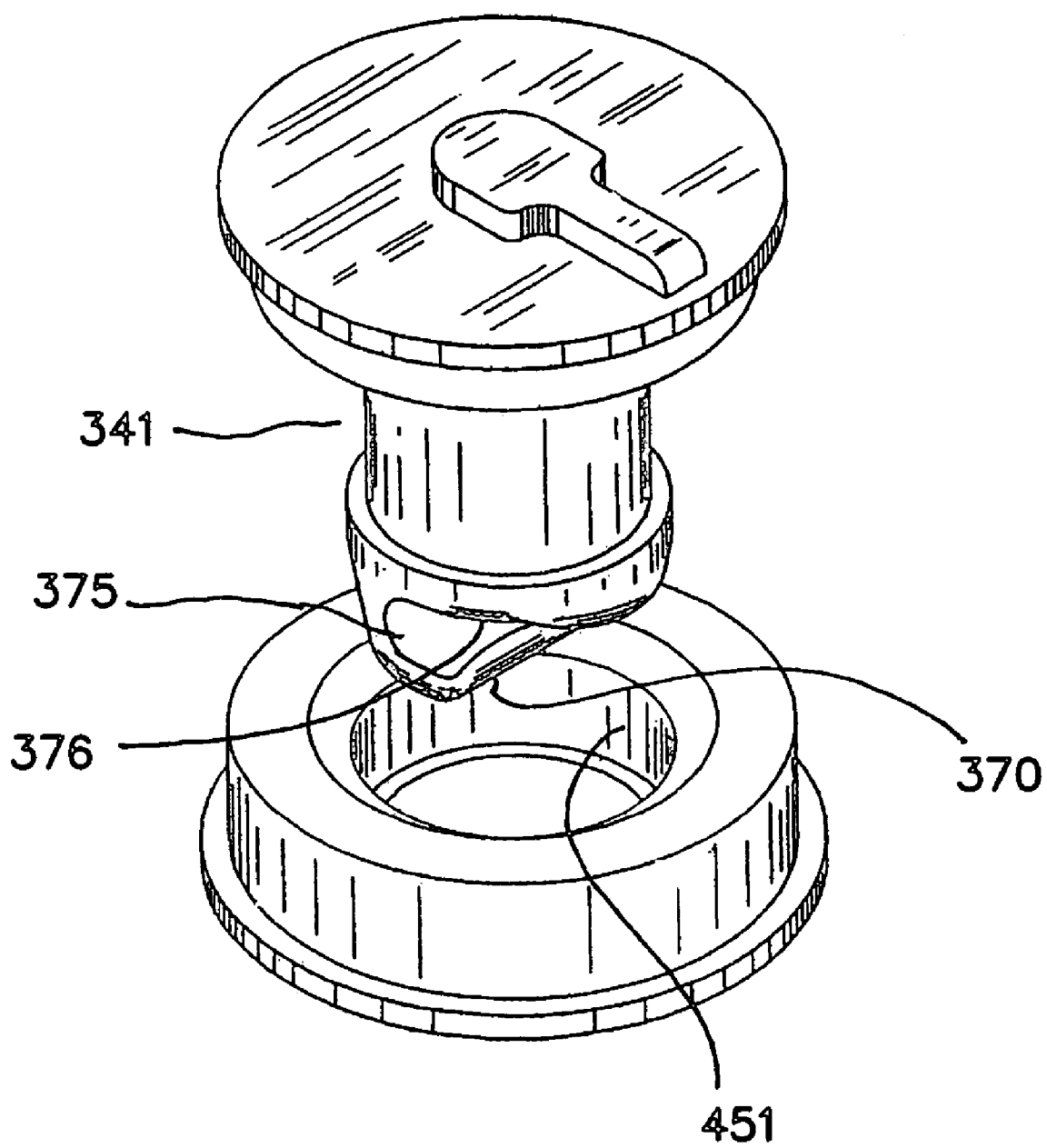
FIG. 6 is another perspective view of the interlocking suture clinch of FIG. 5.

Referring now to FIG. 5, the second interlocking element 400 further comprises a generally ring-shaped body 440 having a proximal end 401 and a distal end 405. The inner portion 450 of the interlocking element 400 is sized and configured to mate with the extending mid-portion 340 of the first interlocking element 300 in a substantially irreversible relationship. A generous radius 420 is associated with the inner portion 450 and the proximal surface 410 of the second interlocking element 400 that also conforms to the radius postulate. A flange 430 may be associated with the distal end 405 of the second interlocking element 400 that is sized and configured to maintain the second element 400 in a preferred position within an applier.

Figure 4:
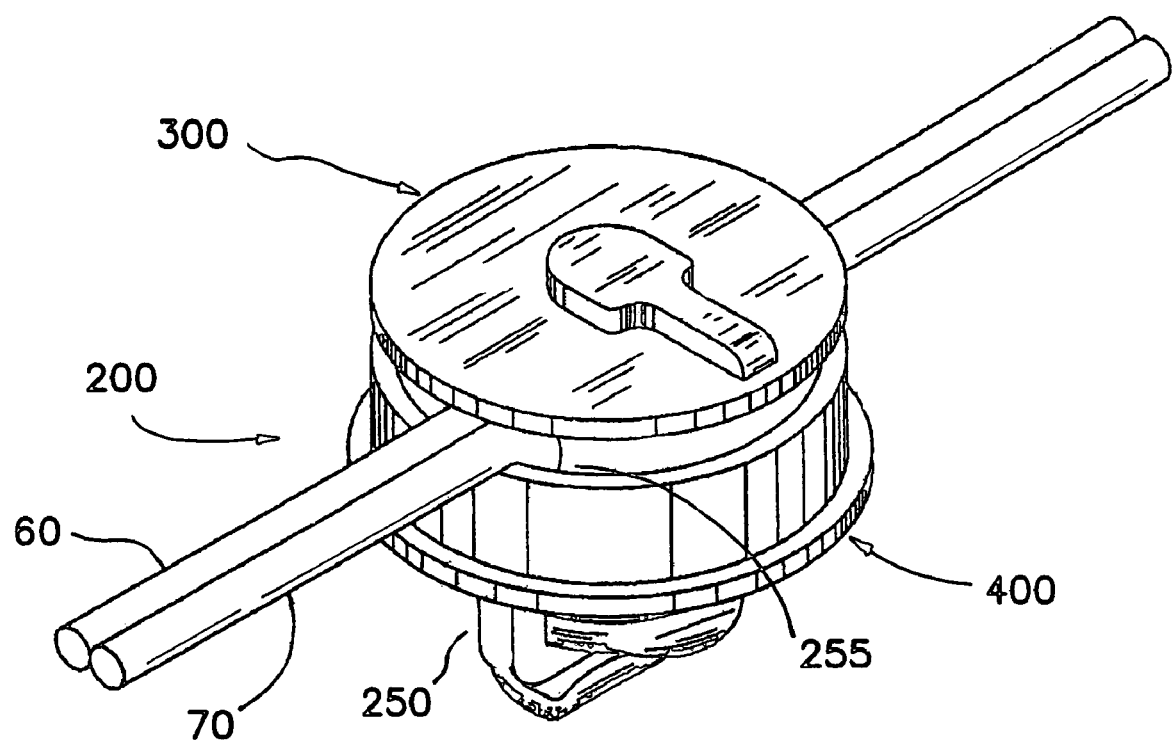
FIG. 4 is a perspective view of an interlocking suture clinch in accordance with a first embodiment of the invention where the interlocking elements are locked together to secure suture strands.

It can be appreciated from FIG. 4 that a length of suture 60 or 70 or lengths of suture 60, 70 are maintained in a severely convoluted condition 250 while in light compression when the two interlocking elements 300, 400 are fully engaged and interlocked. In addition, the pressure exerted upon the interlocking elements 300, 400 as the suture loop 10 (FIGS. 1-3) is tensioned is isolated between the ledge 365 of the distal portion 360 of the first interlocking element 300 and a distal face 465 of the undercut 460 associated with the inner portion 450 of the second interlocking element 400. Therefore, as suture loop 10 is tensioned or tightened, there is no need to over-compress the suture 60, 70 to maintain a secure position for the interlocking suture clinch 200.

Figure 7:
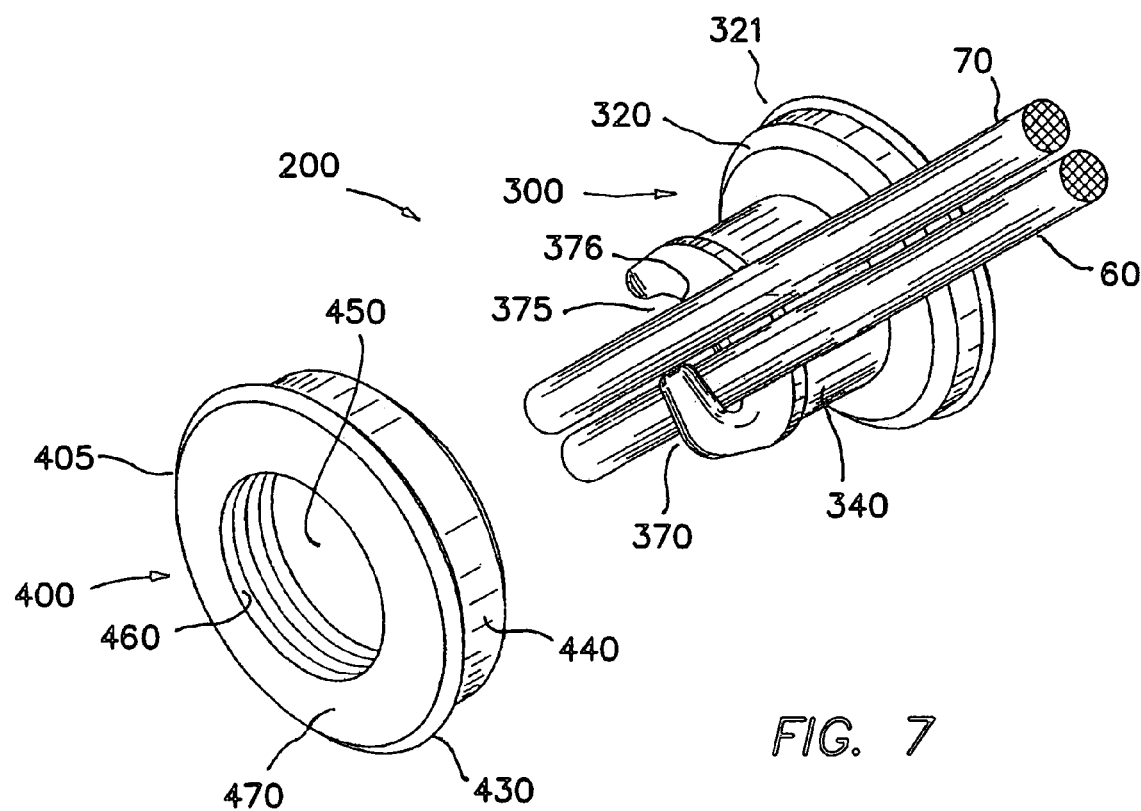
FIG. 7 is a bottom perspective view of the interlocking suture clinch of FIG. 5.
Figure 8:
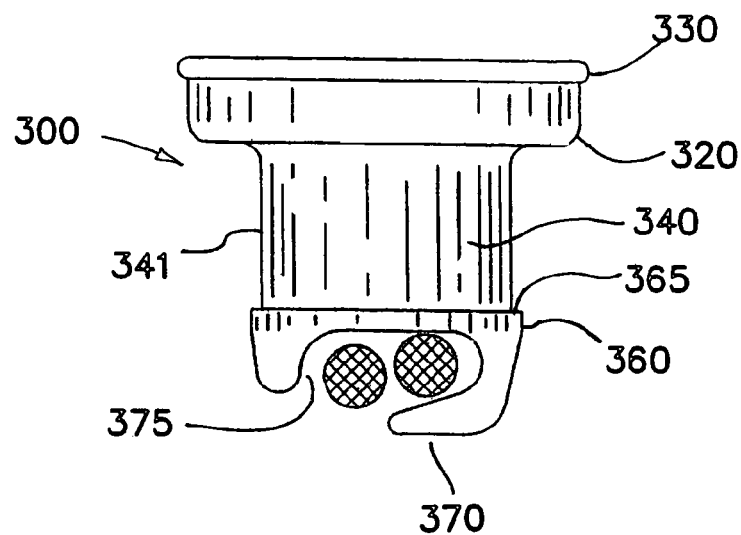
FIG. 8 is a side view of the first interlocking element of the suture clinch with suture extensions in place prior to interlocking.
Figure 9:
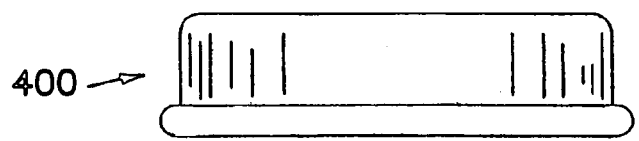
FIG. 9 is a side view of the second interlocking element of the suture clinch prior to interlocking.
Figure 10:
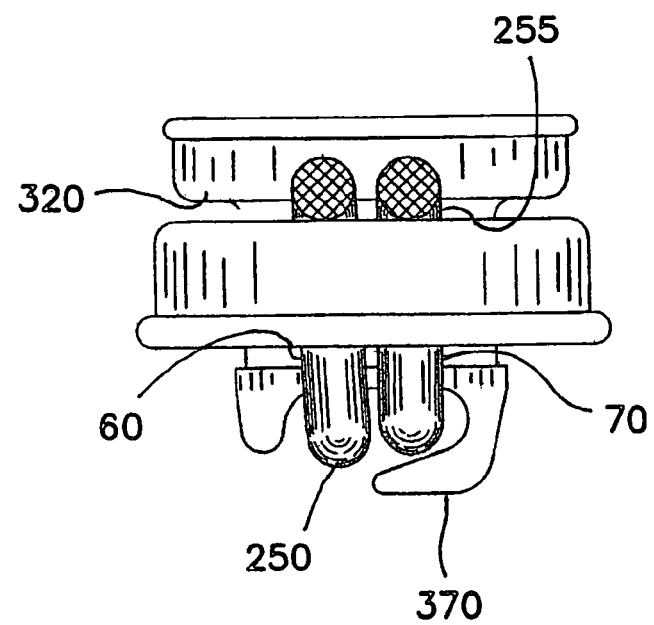
FIG. 10 is a side view of the interlocking suture clinch where the first and second interlocking elements are fully interlocked with suture extensions in place.
Figure 11:
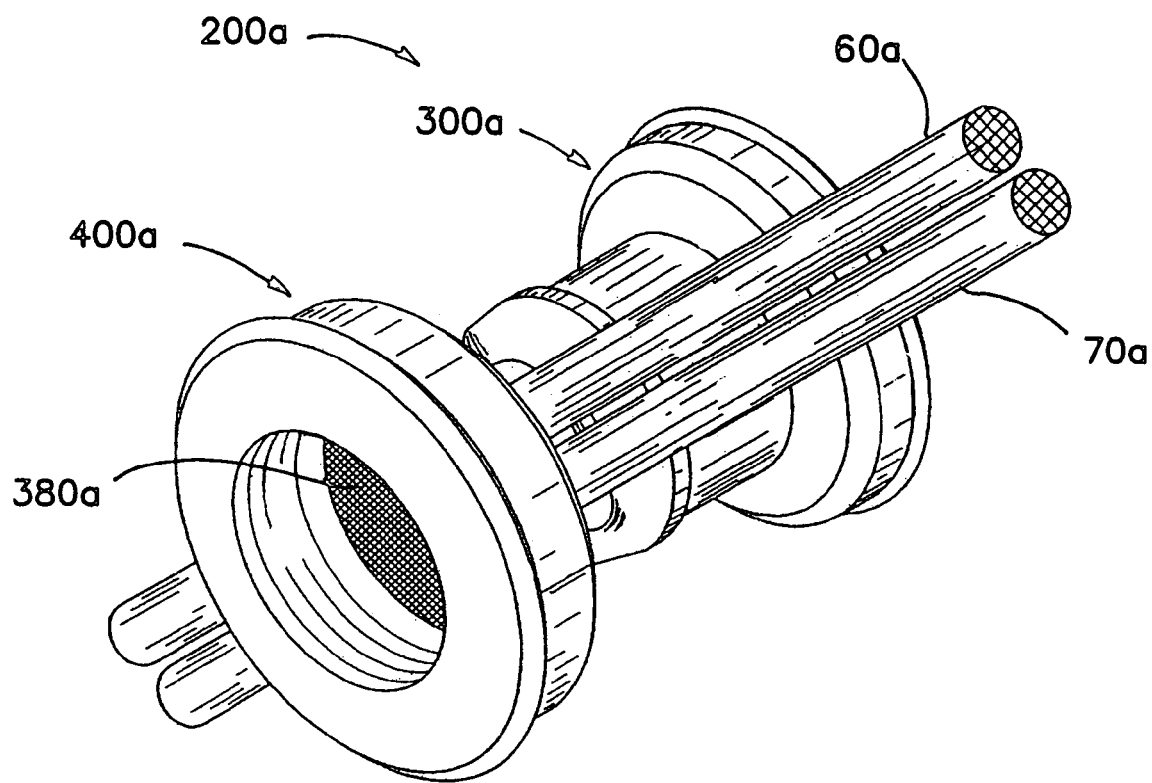
FIG. 11 is a bottom perspective view of the interlocking suture clinch in accordance with another embodiment of the invention where the interlocking elements are pre-assembled in a holding condition.

Referring to FIG. 7, there is shown a bottom perspective view of the interlocking suture clinch 200 including the first interlocking element 300 and the second interlocking element 400 sized and. configured to interlock and securely hold a portion of suture 60, 70. It is especially important to note that suture extensions 60, 70 may be approached and captured obliquely or from the side at an angle. In many cases the application of the interlocking suture clinch 200 must be performed at an angle of less than thirty degrees. In addition, the capturing feature 375 associated with the first interlocking element 300 must contain and hold the suture 60, 70 while the clinch 200 is advanced to the preferred location. This may involve instances where the clinch 200 is applied to the suture extensions 60, 70 at a great distance from the preferred location. Such an instance may involve the need to place the clinch 200 upon the suture extensions outside or external to a laparoscopic site and subsequently advance the clinch through a trocar or access port to the preferred location. It is very important in this scenario that all radii conform to the radius postulate and are as generous as possible. This is especially so in the region of the capturing feature 375 where the suture must make a tortuous bend over a side opening 376 near the distal end 370 of the extending portion 340 of the first interlocking element 300.

Figure 12:
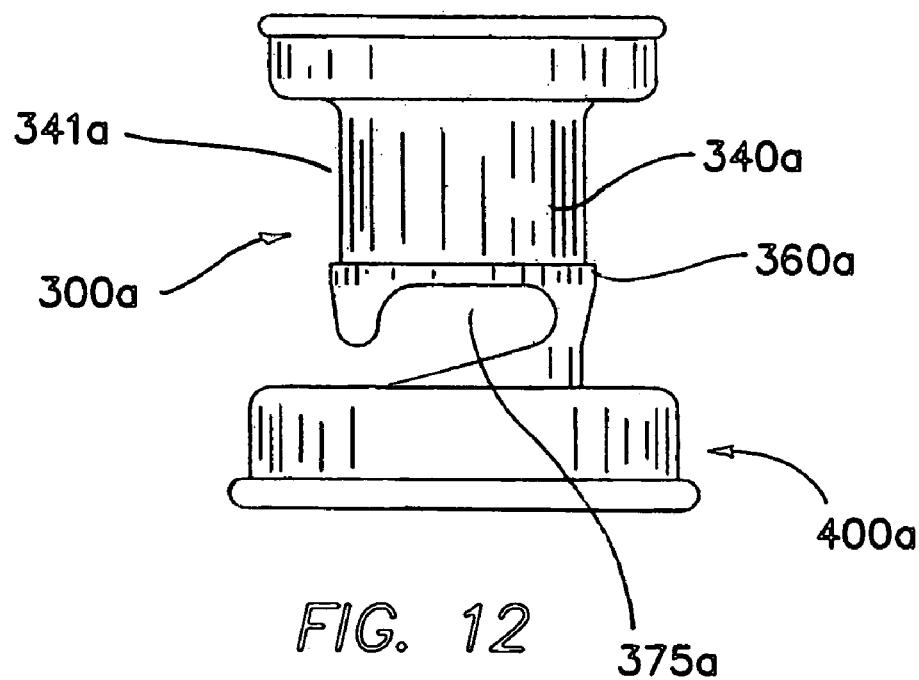
FIG. 12 is a side view of the interlocking suture clinch of FIG. 11.
Figure 13:
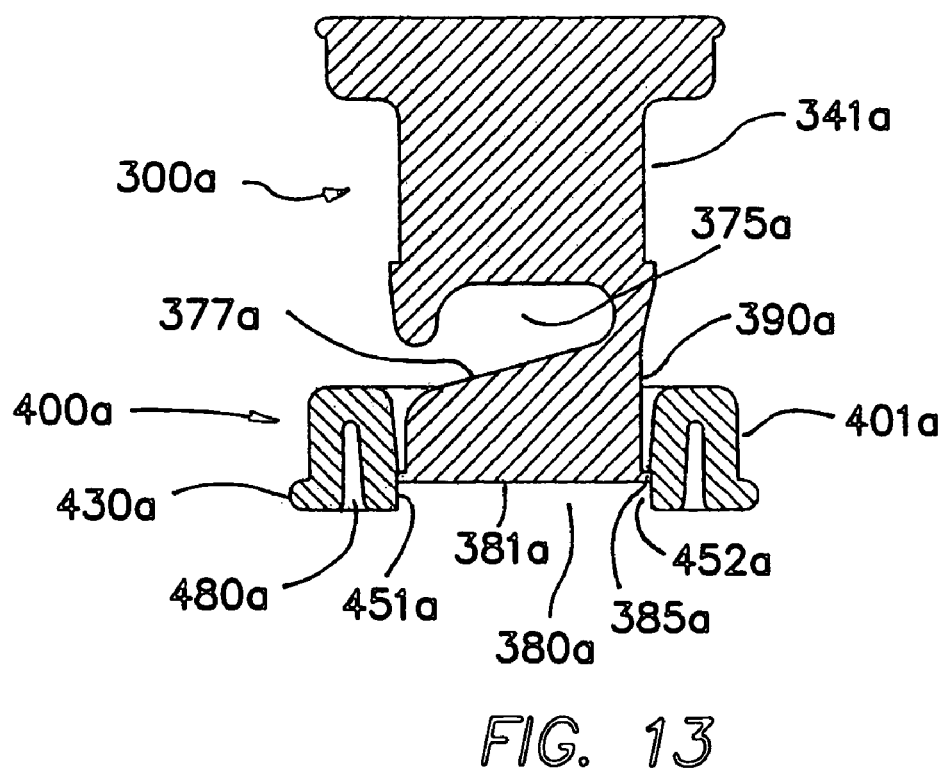
FIG. 13 is a side-section view of the interlocking suture clinch of FIG. 11 where the interlocking elements are pre-assembled in a holding condition.

Referring to FIGS. 11-15, there is shown another embodiment of an interlocking suture clinch 200a of the present invention. Suture clinch 200a comprises a first interlocking element 300a and a second interlocking element 400a. The first interlocking element 300a is sized and configured to fit into the second interlocking element 400a in a substantially irreversible arrangement. The first interlocking element 300a comprises a generally cylindrical body 341a, a proximal end 305a and a distal end 370a. The proximal end 305a is sized and configured to fit into an applier and may comprise an enlarged proximal portion 315a and an alignment feature 311a. The mid-portion 340a of the cylindrical body 341a is sized and configured to exist within the opening 450a of the second interlocking element 400a under no radial compression. Distal to the mid-portion 340a of the cylindrical body 341a is a capturing feature 375a sized and configured to capture and hold at least a length of suture extensions 60a, 70a. Distal to the capturing feature 375a is a retention portion 380a sized and configured to retain the first interlocking element 300a within the second interlocking element 400a in a first, pre-compressed condition as illustrated in FIGS. 12 and 13.

The retention portion 380a further comprises an enlargement 385a at a distal end 381a of the cylindrical body 341a that engages an undercut 485a (see, e.g., FIGS. 15A-15C) associated with the opening 450a of the second interlocking element 400a. The enlargement 385a is circumferential and may comprise a continuous feature or may be interrupted, resembling teeth, pins or cogs. The second interlocking element 400a is sized and configured to retain the first interlocking element 300a in a one-way relationship. The undercut 485a is further associated with inner wall 451a of the second interlocking element 400a that allows the first interlocking element 300a to move in one direction only, i.e., distally. In addition, a compression relief 480a may be provided in a ring-shaped body 401a of the second interlocking element 400a to allow the material of the ring-shaped body 401a to exist in a pre-assembled condition under an appropriate compressive load 301a. Additionally, the compression relief 480a allows the ring-shaped interlocking element 400a to be produced with a drafted or angled undercut 452a that further retains the retention portion or enlargement 385a of the first interlocking element 300a in a bidirectional arrangement. The compression relief 480a, moreover, reduces the compressive load upon suture extensions 60a, 70a within the assembled suture clinch 200a and compensates for varying suture 60a, 70a diameters.

Referring to FIGS. 14A-14C, the interlocking suture clinch 200a is shown in a progressive series where the pre-assembled clinch 200 is initially placed adjacent to suture extensions 60a, 70a, which are subsequently captured within a capturing feature 375a. Next, the interlocking suture clinch 200a is partially compressed to a second condition as shown in FIG. 14B where side opening 376a of capturing feature 375a is within opening 450a of the second, ring-shaped interlocking element 400a. The interlocking suture clinch 200, as shown in FIG. 14B, is fully engaged to suture extensions 60a, 70a in a sliding or adjustable relationship. The clinch 200a may be easily advanced to a desired position with no damage to suture extensions 60a, 70a. When clinch 200a has been advanced to the desired position, it may be further compressed to a final condition where a ledge 365a associated with the cylindrical body 341a of the first interlocking element is retained by a distal face 470a of the second interlocking element 400a. In the final condition as shown in FIG. 14C, the clinch 200a retains suture extensions 60a, 70a in a tortuous pathway.

Figure 15A:
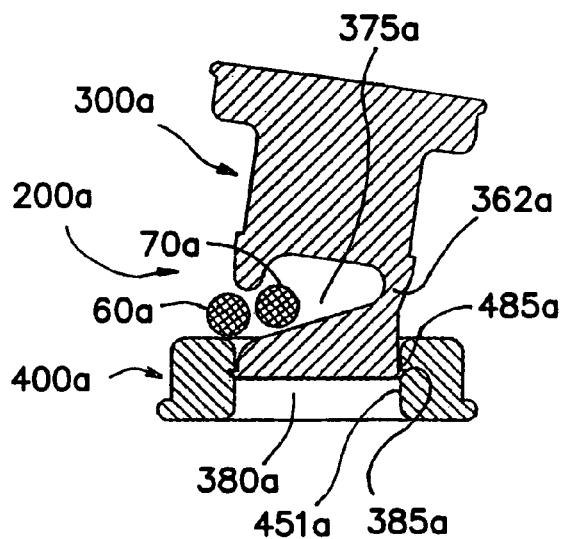
FIGS. 15A-15D illustrate side-section, series views of an interlocking suture clinch where the interlocking elements are pre-assembled in a holding condition and further comprising a deformable portion in accordance with another embodiment of the invention.
Figure 15B:
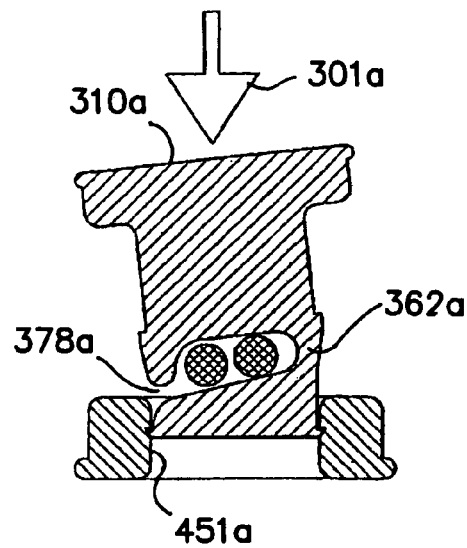

Referring to FIGS. 15A-15D, it may be seen that a portion 362a of the capturing feature 375a associated with the first interlocking element 300a may be deformable. In a first retained condition as illustrated in FIG. 15A, the pre-assembled suture clinch 200a may be held in an applier by the first interlocking element 300a. The second interlocking element 400a may be allowed to move in response to the introduction of suture extensions 60a, 70a due to the deformable portion 362a associated with the first interlocking element 300a thereby creating an enlarged capturing feature 375a. As compressive load 301a is subsequently placed upon the first and second interlocking elements, the capturing feature 375a associated with the first interlocking element 300a is deformed into a substantially closed condition as illustrated in FIG. 15B, thereby temporarily securing the suture extensions 60a, 70a.

Figure 15C:
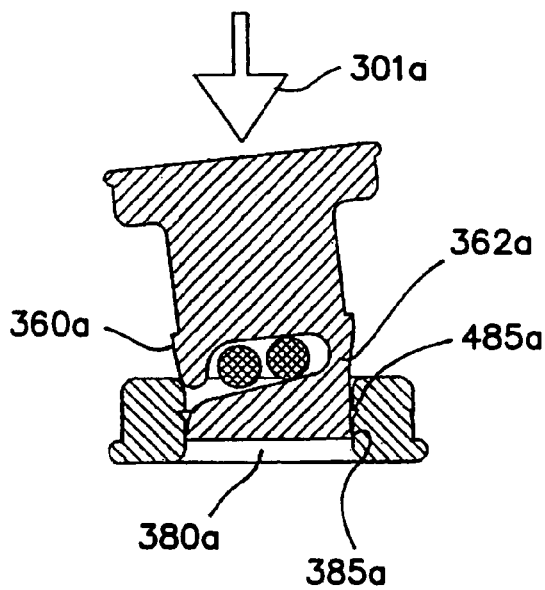
Figure 15D:
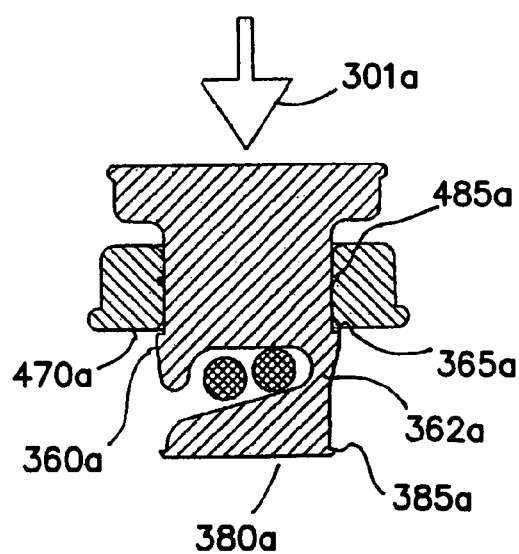
Figure 16:
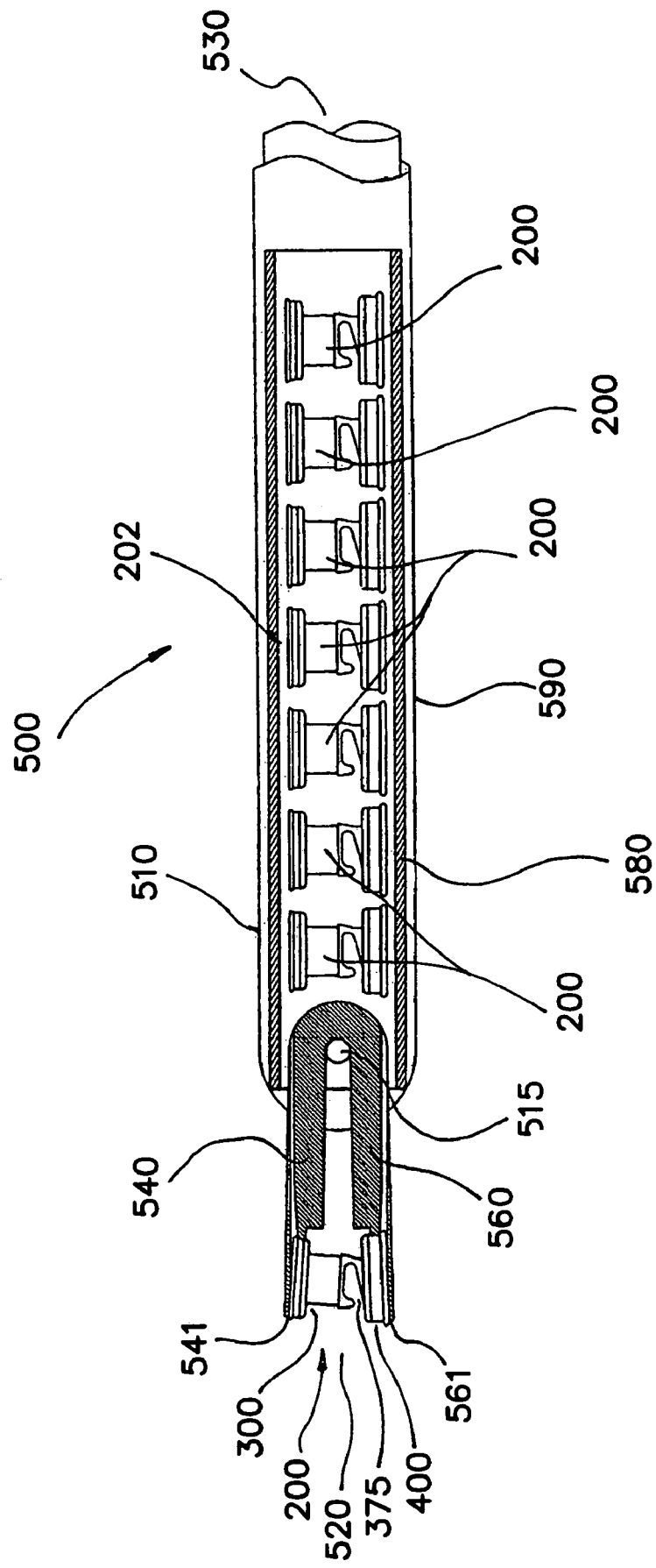
FIG. 16 is a side-section view of an interlocking clinch applier of the invention.
Figure 17:
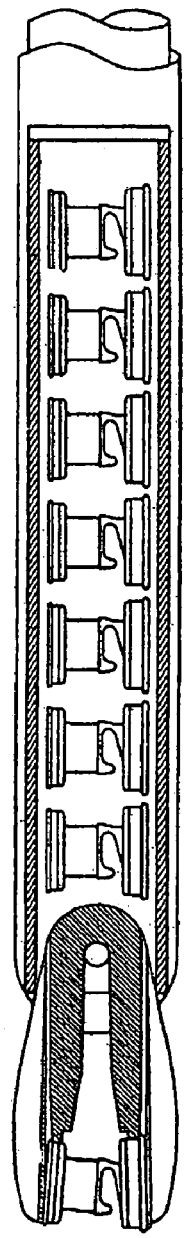
FIG. 17 is a side-section view of the clinch applier of FIG. 16 in a first, holding and open condition.
Figure 18:
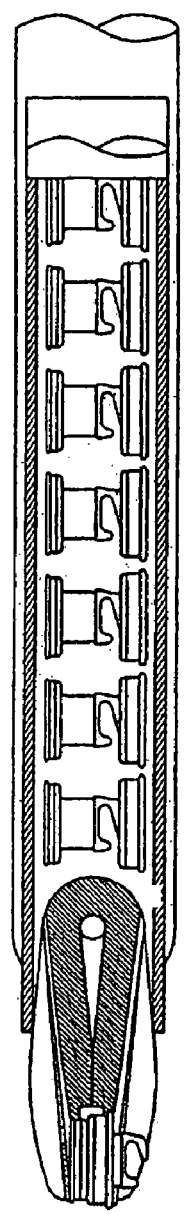
FIG. 18 is a side-section view of the clinch applier of FIG. 16 in a second, closed condition.
Figure 19:
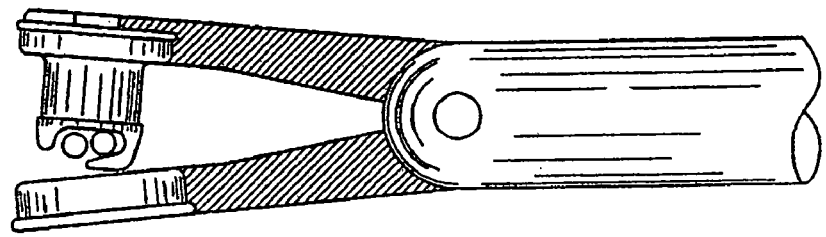
FIG. 19 is a side-section view of the distal end portion of a complex, hinged applier.
Figure 20:
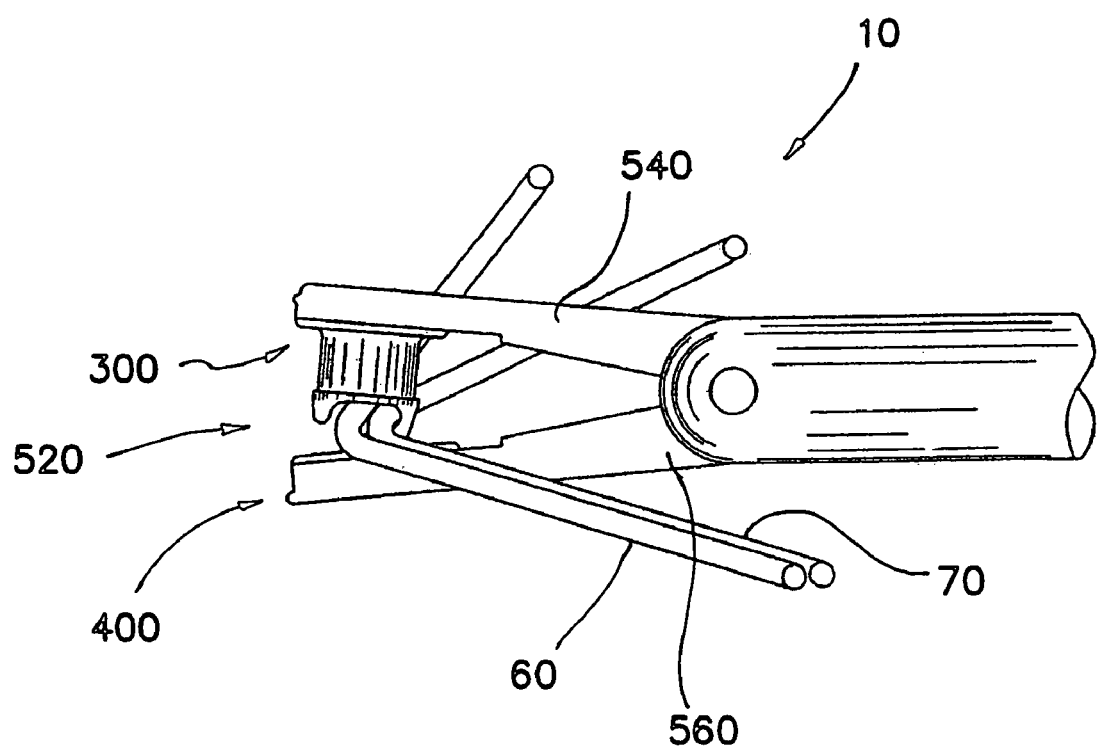
FIG. 20 is a side view of the distal end portion of a complex, hinged applier further illustrating the position of suture extensions within the suture clinch and jaws of the applier.

Next, the compressive load 301a is increased to dislodge the enlargement 385a associated with the first interlocking element 300a from the undercut 485a associated with the second interlocking element 400a and place the interlocking elements 300a, 400a in a condition as illustrated in FIG. 15C where they may be advanced to a desired position along the suture extensions 60a, 70a. Finally, the compressive load 301a may be increased to fully interlock the two interlocking elements 300a, 400a where the enlargement 385a associated with the cylindrical body 341a of the first interlocking element 300a is beyond the distal face 470a of the second interlocking element 400a. It is further contemplated that the ledge 365a associated with the enlargement 360a of the cylindrical body 341a of the first interlocking element 400a be substantially larger and more secure than the retention feature 385a associated with the distal retention portion 380a of the first interlocking element 300a.

Referring to FIGS. 16-20, there is shown an applier 500 including jaws 540, 560 of the invention for use with an interlocking suture clinch 200 in its simplest form. It is appreciated that a variety of mechanisms may be employed to close the jaws 540, 560 of applier 500. For the sake of clarity, a simple closing mechanism is illustrated so that the function of suture clinch 200 may be appreciated fully. Applier 500 further comprises an elongate body 510, a proximal end 530 and a distal end 520. The body 510 is preferably tubular and may contain working elements for actuation and a plurality of stored suture clinches 200. The proximal end 530 may comprise a handle to be held by a user. The handle may take the form of a "pistol grip" with opposing handle elements or it may comprise an "in-line" arrangement where a slide, lever or plunger is employed to actuate elements associated with the distal end 520 of the applier 500. The distal end 520 of the applier 500, in a preferred embodiment, comprises opposing jaw members 540, 560. At least one of the jaw members 540, 560 is movable in response to actuation from the actuation elements associated with the handle at the proximal end 530 of the applier 500.

In one embodiment, a first interlocking suture clinch element 300 is placed within the first jaw member 540 of applier 500. The second interlocking suture clinch element 400 is placed within the second jaw member 560 of applier 500. The interlocking suture clinch 200 thus held may be advanced to engage suture extensions 60, 70 and capture the extensions 60, 70 in capturing feature 375 associated with the first interlocking clinch element 300. The jaws 540, 560 of applier 500 may subsequently be compressed to close or compress the associated interlocking suture clinch 200. The fully compressed and interlocked suture clinch 200 is urged from the jaws 540, 560 and subsequently released. The release openings 541, 561 in the jaws may be associated with the distal ends of jaws 540, 560 or may be associated with a side portion of the jaws 540, 560. In addition, the jaws 540, 560 may be straight, "in-line" or they may be angled from the axis of the elongate body 510 of applier 500. The simplest form of the mechanism contemplated for actuation of the jaws 540, 560 may include an inner tube 580 coaxial to the tubular, elongate body 510 of the applier 500. The inner tube 580 may be advanced over the open jaws 540, 560 to force them into a closed, compressed condition.

It is also contemplated by the present invention that a hinge 515 or plurality of hinges and hinged arms be employed to provide leveraged advantages to the closing mechanism. It is further contemplated that the jaws 540, 560 be discrete, individual hinged elements cooperating with actuation elements associated with the proximal handle of the applier 500. It is further contemplated that the first jaw 540 is movable in response to actuation elements associated with the proximal handle and the second jaw 560 is fixed so that it remains in a fixed relationship with the elongate body 510 of the applier 500. Alternately, the first jaw 540 may be fixed in relationship to the elongate body 510 of the applier 500 and the second jaw 560 may be movable in response to actuation elements associated with the handle at the proximal end of the applier 500. Associating a fixed first jaw 540 with a first interlocking pre-assembled suture clinch element 300 may provide the advantage that the opposing jaws 540, 560 need not be accurately aligned for placement of the first interlocking clinch element 300 into the opening 450 of the second interlocking element 400. The pre-assembled clinch 200 may be attached or held within the first jaw member 540 and subsequently compressed by an opposing second jaw member 560.

It is further contemplated that a plurality of interlocking suture clinches 200 are stored within the elongate body 510 of the applier 500 and are either manually or automatically dispensed into the clinch holding features associated with the jaws 540, 560 of the applier 500. In one aspect of the invention, the interlocking suture clinch 200 may comprise a cartridge that holds a plurality of clinch elements in an arrangement for advancement to the jaws 540, 560 of the applier 500. Additionally, the suture clinches 200 may be manufactured in a connected arrangement as illustrated in FIGS. 21 and 22 such that a plurality of clinches 200 exist as a unit 601, 651 and are advanced by pressure upon the proximal end 602, 652 of the unit 600, 650, respectively. In the case of pre-assembled interlocking suture clinches 650 (see, e.g., FIG. 22) manufactured according to the "unit" structure, the two interlocking suture clinch units 300, 400 may be partially assembled and placed within the elongate body 510 of the applier 500. Another embodiment of the invention includes the incorporation of interlocking suture clinches 200 into cartridges sized and configured to hold the clinches 200 in a desired condition such that an applier 500 may approach the clinches 200 and insert them into jaw pockets associated with the jaws 540, 560 of applier 500.

Figure 23:
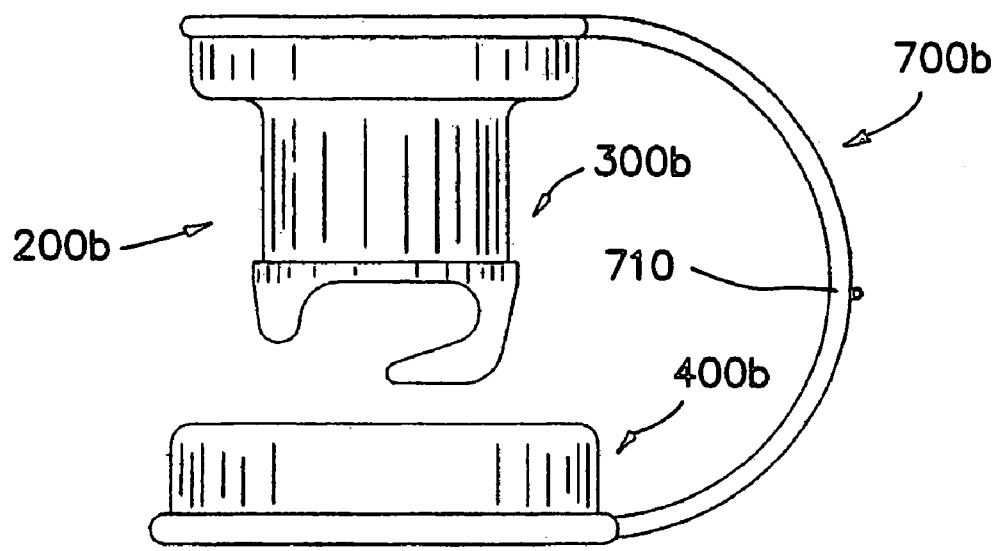
FIG. 23 is a side view of a preferred embodiment of the interlocking suture clinch further comprising a tether between a first interlocking element and a second interlocking element.
Figure 24:
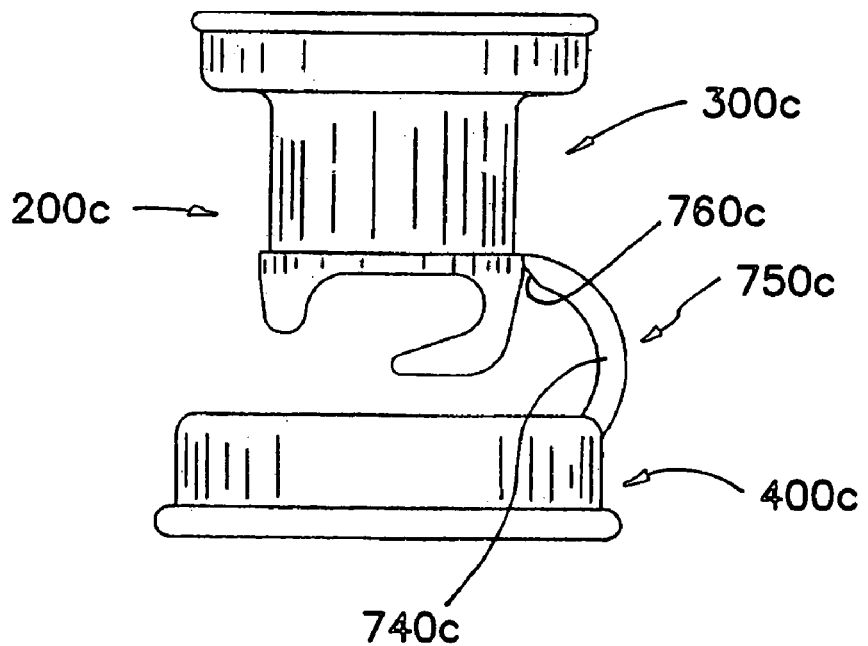
FIG. 24 is a side view of another preferred embodiment of the interlocking suture clinch further comprising a "living hinge" between a first interlocking element and a second interlocking element.
Figure 27:
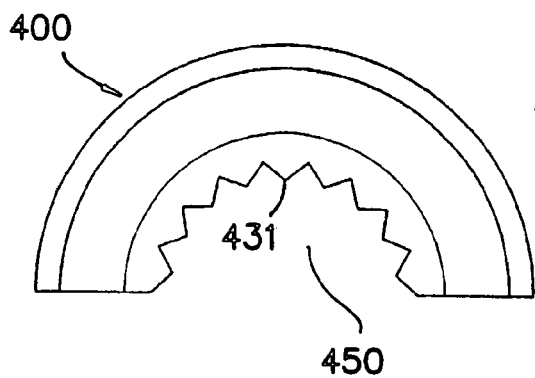
FIG. 27 is a top view of a section of the second interlocking element of a suture clinch illustrating a preferred surface condition within the opening of the second interlocking element.
Figure 28A:
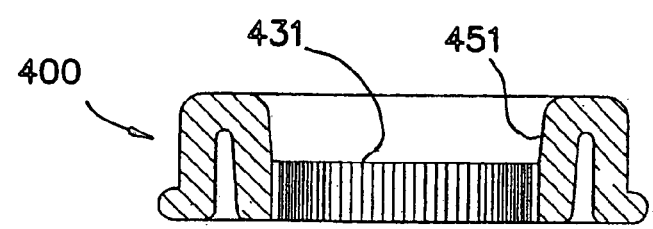
FIGS. 28A-28D are side-section views of the second, ring-shaped, interlocking element illustrating alternate surface conditions to enhance traction upon the suture.
Figure 28B:
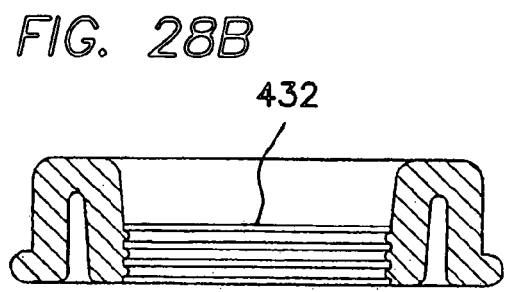
Figure 28C:
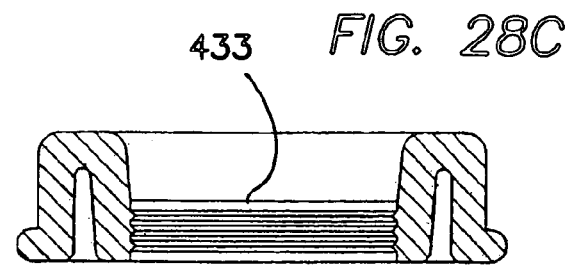
Figure 28D:
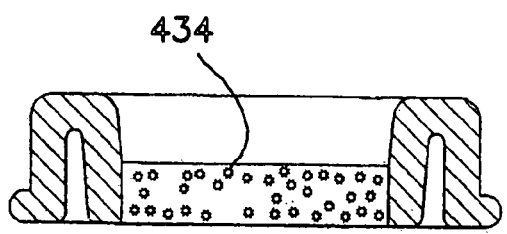
Figure 29:
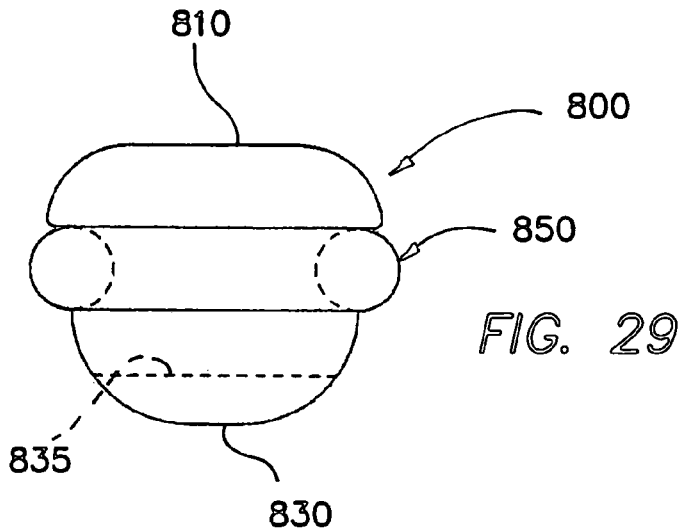
FIG. 29 is a side view of an interlocking suture clinch in accordance with another embodiment of the invention having a rigid element and an elastomeric element.
Figure 30:
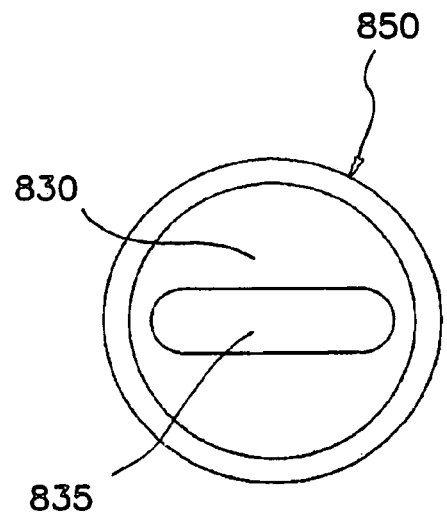
FIG. 30 is a bottom view of the interlocking suture clinch of FIG. 29 having a rigid element and an elastomeric element.
Figure 32:
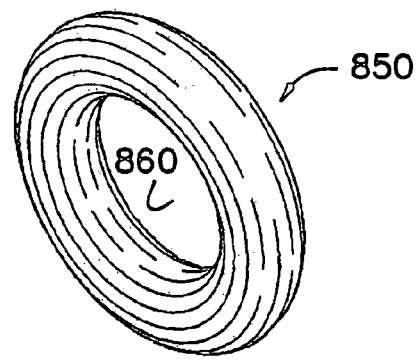
FIG. 32 is a perspective view of the rigid element associated with the suture clinch of FIG. 29.
Figure 31:
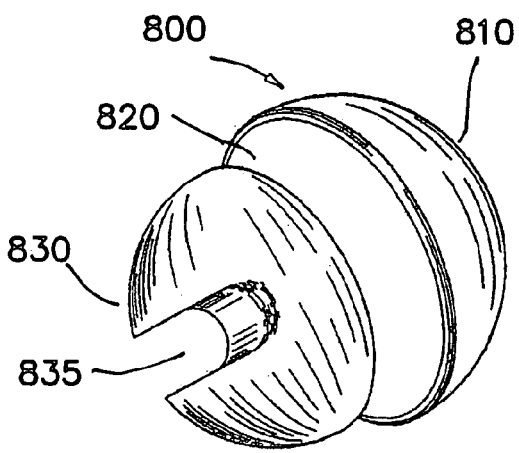
FIG. 31 is a perspective view of the elastomeric element associated with the suture clinch of FIG. 29.
Figure 33:
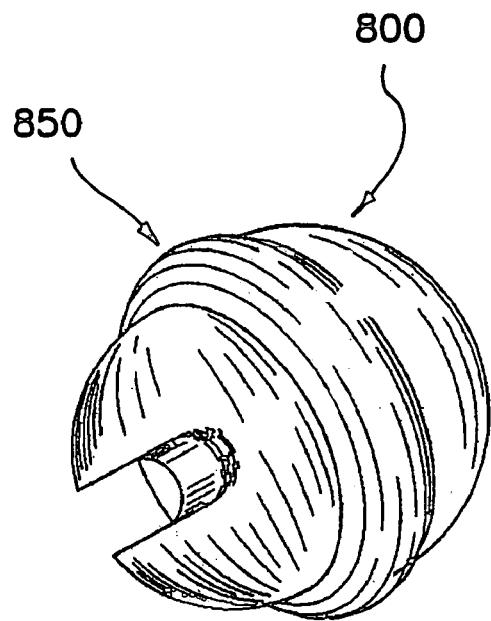
FIG. 33 is a perspective view of the elastomeric element and the rigid element associated with the suture clinch of FIG. 29 combined with each other.
Figure 34:
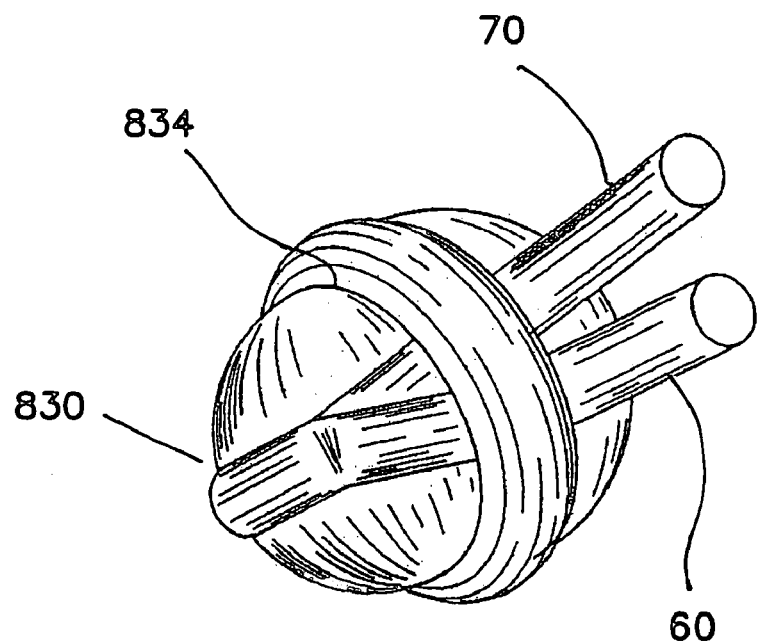
FIG. 34 is a perspective view of the elastomeric element and the rigid element associated with the suture clinch of FIG. 29 combined with each other and further having two strands of suture within the holding portion.

Referring to FIG. 23, a suture clinch 200b according to another embodiment of the invention is shown comprising a first interlocking element 300b, a second interlocking element 400b and a tether 700b between the first interlocking element 300b and the second interlocking element 400b. The tether 700b is sized and configured to retain the first and second elements 300b, 400b in a desired position and orientation for introduction into an applier and to maintain a desired arrangement for capturing suture extensions. The tether 700b is preferably formed when the first and second elements 300b, 400b are formed. The tether 700b may remain after the suture clinch 200b is placed or it may be severed and removed. In yet another embodiment of the invention as shown in FIG. 24, a suture clinch 200c may comprise a living hinge 750c between a first interlocking element 300c and a second interlocking element 400c. The living hinge 750c may be formed as the first and second interlocking elements 300c, 400c are formed. The living hinge 750c comprises a material connection 740c formed between the first and second elements 300c, 400c having a deformable portion 760c sized and configured to bend or deform in a preferred manner. Such a living hinge 750c may be configured to provide flexibility in a single plane while maintaining alignment in the opposite plane.

Referring to FIGS. 25 and 26, there are shown additional embodiments of the present invention comprising a plurality of retaining features 395d, 495d associated with mating or adjoining portions of first and second interlocking elements 300d, 400d. The plurality of retaining features 395d, 495d serve to retain the position of the interlocking elements 300d, 400d in a desired condition or position. The first interlocking element 300d may be compressed into the second interlocking element 400d to a point corresponding to a specific suture 60d, 70d diameter or type. An alternate embodiment comprising a pre-assembled interlocking suture clinch may make use of a plurality of retaining features 395d, 495d to, first, hold the two interlocking elements 300d, 400d in a desired condition or position prior to compression (FIG. 26A) and, second, retain the first and second interlocking elements 300d, 400d in a desired state of compression (FIG. 26B) that compensates for varying suture 60d, 70d diameter or type. The retaining features 395d, 495d generally comprise tapered angular mating slots 396d and ridges 496d resembling a one-way ratchet.

FIGS. 27 and 28A-28D illustrate various surface conditions that may be incorporated in the inner wall 451 of the opening 450 of the second interlocking element 400. In particular, the surface conditions may comprise axial ridges or slots 431, circumferential nodes 432, circumferential ridges or slots 433, random deformations, bumps, pits, burrs or embossed patterns or features 434.

Referring to FIGS. 29-34, there is shown another embodiment of the invention comprising a first interlocking element 800 and a second interlocking element 850. The first interlocking element 800 further comprises a substantially spherically shaped member having a proximal first portion 810, a reduced diameter mid-portion or waist 820 and an enlarged distal second-portion 830. The second interlocking element 850 further comprises a ring that is sized and configured to fit neatly into the reduced diameter mid-portion or waist 820 of the first interlocking element 800 and remain there. The first interlocking element 800 is preferably constructed of an elastomeric material. The second interlocking element 850 is preferably constructed of a rigid material. The extensions of suture 60, 70 placed through a tissue are engaged by a slot 835 in the distal portion 830 of the first interlocking element 800 and subsequently pressed through an opening 860 in the second interlocking element 850.

A movable, sliding relationship exists between the suture extensions 60, 70 and the interlocked suture clinch until the first interlocking element 800 is fully pressed into the second interlocking element 850 so that the second, ring-shaped interlocking element 850 is fully within the reduced diameter mid-portion or waist 820 of the first interlocking element 800. A cross-pull between the suture extensions 60, 70 and the suture loop 10 (see, e.g., FIGS. 2 and 3) results in a deformation of the elastomeric material at the distal interface 834 of the first interlocking element 800 and the second interlocking element 850, preventing the first interlocking element 800 from passing through the opening 860 of the second, ring-shaped interlocking element 850.

A feature of this embodiment is the capturing of suture extensions 60, 70 by waist 820, which is constructed of an elastomeric material, against an inner surface of interlocking element 850, which is constructed of a rigid material. In particular, the elastomeric material of waist 820 operates to "grab" or encapsulate a portion of suture extensions 60, 70 against the inner surface of interlocking element 850 thereby increasing the holding function and resistance to suture movement while protecting suture extensions 60, 70 from any deformation or notching damage.

The foregoing disclosure and description of the invention are illustrative and explanatory thereof, and various changes in the size, shape and materials, as well as in the details of the illustrated construction, may be made without departing from the scope and spirit of the invention.

The invention claimed is:

1. A suture securing device comprising:
   a male piece having a flanged top portion, a center shaft having a proximal end and a distal end, the proximal end of the center shaft being connected to the flanged top portion, and an end member connected to the distal end of the center shaft, the end member having a capturing feature away from the center shaft, the capturing feature comprising a hook member having a first sidewall, said first sidewall is parallel to said flanged top portion a second sidewall offset from generally parallel to and facing the first sidewall, a recess formed between the first sidewall and the second sidewall adapted to receive a suture, and a projection extending transversely from the first sidewall; and
   a female piece having a top, proximal end and a bottom, distal end comprising a column being generally cylindrical in shape and forming a hollow opening along its length,
   wherein said opening slidingly receives said center shaft and a suture to be captured and held by said capturing feature, said suture being secured in place between said column and said center shaft such that the suture follows a pathway defined by the male piece and the female piece, the pathway extending on a first side between the flanged top portion of the male piece and the proximal end of the female piece, between the center shaft and the column past the distal end of the female piece, through the capturing feature, and on a second side generally opposite the first side between the center shaft and the column and between the flanged top portion of the male piece and the proximal end of the female piece, said center shaft of the male piece having a length greater than the length of the female piece.

2. The securing device of claim 1, wherein the assembled male piece and female piece are irreversibly interlocked.

3. The securing device of claim 1, wherein the suture includes a pair of suture extensions.

4. The securing device of claim 1, wherein the pathway defined by the assembled male piece and female piece comprises a lightly compressed, convoluted or tortuous pathway.

5. The securing device of claim 1, wherein the capturing feature is formed to engage and obliquely capture the suture from different angles.

6. The securing device of claim 5, wherein the capturing feature is formed into a hook, the hook having a deformable middle portion aligned with the center shaft in a first position and movable out of alignment with the center shaft in a second position.

7. The securing device of claim 5, wherein the angle is less than thirty degrees.

8. The securing device of claim 1, wherein the top portion further comprises a flat portion and an alignment feature for aligning the male piece in an applier.

9. The securing device of claim 1, wherein the end member of the male piece further comprises a ledge for mating with an undercut in a distal portion of the female piece when the male piece and the female piece are fully engaged and compressed.

10. The securing device of claim 1, wherein the center shaft further comprises a reduced diameter section to allow the suture to be placed between the column and the center shaft without damage to the suture.

11. The securing device of claim 9, wherein the female piece further comprises a flange at the distal end for aligning the female piece in an applier.

12. The securing device of claim 1, wherein radii of the male piece and the female piece are greater than the radius of the suture.

13. The securing device of claim 9, wherein the capturing feature further comprises a retention portion at a distal end of the capturing feature to retain the male piece within the female piece in a pre-compressed condition, the capturing feature positioned between the retention portion and the center shaft.

14. The securing device of claim 13, wherein the retention portion further comprises an enlargement that engages an undercut within the opening of the female piece.

15. The securing device of claim 14, wherein the enlargement includes teeth, pins or cogs.

16. The securing device of claim 14, wherein the undercut allows the male piece to move in one direction only.

17. The securing device of claim 1, wherein the female piece further comprises a ring-shaped compression relief that allows bi-directional movement of the male piece within the opening of the female piece.

18. The securing device of claim 17, wherein the compression relief reduces the compressive load upon the suture within the assembled male piece and female piece and compensates for varying suture diameters, the ring-shaped compression relief encircling the opening of the female piece.

19. The securing device of claim 17, wherein the ring-shaped compression relief separates an inner wall of the female piece and an outer wall of the female piece.

20. The securing device of claim 1, further comprising a link formed between the male piece 300 and the female piece 400.

21. The securing device of claim 20, wherein the link is a tether 700b.

22. The securing device of claim 20, wherein the link is formed when the male piece 300 and the female piece 400 are formed.

23. The securing device of claim 20, wherein the link is attached to the top portion 310 of the male piece 300 and the bottom end of the female piece 400.

24. The securing device of claim 20, wherein the link is attached to the capturing feature 375 and the top end of the female piece 400.

25. The securing device of claim 20, wherein the link is severed and removed after placement and assembling of the male piece 300 and the female piece 400.

26. The securing device of claim 20, wherein the link is formed of a deformable material to provide flexibility in one plane while maintaining alignment in an opposite plane.

27. The securing device of claim 1, wherein the center shaft of the male piece further comprises a retaining feature to retain the male piece in a desired position in the opening of the female piece.

28. The securing device of claim 27, wherein the opening further comprises a corresponding retaining feature to mate with the retaining feature of the male piece.

29. The securing device of claim 28, wherein the retaining features of the male piece and the female piece together compensate for varying suture diameter or type.

30. The securing device of claim 28, wherein the retaining feature of the male piece comprises a tapered angular mating slot and the corresponding retaining feature of the female piece comprises a ridge resembling a one-way ratchet.

31. The securing device of claim 1, wherein the hollow opening forms an inner wall comprising at least one of a plurality of axial ridges or slots, circumferential nodes, circumferential ridges or slots, random deformations, bumps, pits, and burrs or embossed patterns or features.

32. The securing device of claim 1, further comprising a plurality of identical securing devices produced according to the process of forming the securing devices in a linear sequence wherein the securing devices is separably connected to one another.

33. A method for applying a suture securing device, comprising the steps of:
providing the suture securing device comprising a male piece having a flanged top portion, a center shaft having a proximal end and a distal end, the proximal end of the center shaft being connected to the flanged top portion, and an end member connected to the distal end of the center shaft, the end member having a capturing feature away from the center shaft, the capturing feature comprising a hook member having a first sidewall, said first sidewall is parallel to said flanged top portion a second sidewall offset from generally parallel to and facing the first sidewall, a recess formed between the first sidewall and the second sidewall adapted to receive a suture, and a projection extending transversely from the first sidewall; and a female piece having a top, proximal end and a bottom, distal end comprising a column being generally cylindrical in shape and forming a hollow opening along its length, wherein said opening slidingly receives the center shaft and a suture to be captured and held by said capturing feature, said suture being secured in place between said column and said center shaft;
aligning the male piece and the female piece at a desired location for applying the suture securing device;
pressing the center shaft of the male piece into the opening of the female piece; and
continuing to press the center shaft of the male piece into the opening of the female piece until a portion of the center shaft and the capturing feature extends through the opening and beyond the bottom end of the female piece such that the suture follows a pathway defined by the male piece and the female piece, the pathway extending on a first side between the flanged top portion of the male piece and the proximal end of the female piece, between the center shaft and the column past the distal end of the female piece, through the capturing feature, and on a second side generally opposite the first side between the center shaft and the column and between the flanged top portion of the male piece and the proximal end of the female piece.

34. The method of claim 33, further comprising the step of applying a compressive load on the male piece to dislodge an enlargement from an undercut of the female piece and to place the male piece and the female piece in a condition where they may be advanced to a desired position along the suture.

35. The method of claim 33, wherein the assembled male piece and female piece are irreversibly interlocked.

36. The method of claim 33, wherein the assembled male piece and female piece form a lightly compressed, convoluted or tortuous pathway.

37. The method of claim 33, wherein the capturing feature is formed into a hook delimiting an aperture and further comprising enlarging the aperture of the hook.

38. The method of claim 33, wherein the capturing feature is formed into a hook with a deformable portion and further comprising pivoting the female piece away from the male piece about the deformable portion of the hook.

39. A suture securing device comprising:
a male piece having:
a flanged top portion with a proximal end and a distal end,
a cylindrical center shaft with a proximal end and a distal end, the proximal end of the cylindrical center shaft connected to the distal end of the flanged top portion,
a hook-like capturing feature having a proximal end and a distal end, the hook-like capturing feature comprising a first sidewall, said first sidewall is parallel to said flanged top portion a second sidewall offset from and, generally parallel to and facing the first sidewall, a recess formed between the first sidewall and the second sidewall adapted to receive a suture, and a projection extending transfersely from the first sidewall, the proximinal end of the hook-like capturing feature connected to the distal end of the cylindrical shaft,
a ledge positioned between the proximal end of hook-like capturing feature and the distal end of the cylindrical center shafter; and
a female peice having a top, proximal end and a bottom, distal end comprising a ring with a cylindrical hollow opening axially aligned with the cylindrical center shaft and extending completely through the female piece from the top end to the bottom end, the opening slidingly receives the center shaft and the suture to be captured and held by the capturing feature such that the suture follows a pathway defined by the male piece and the female piece, the pathway extending a first side between the flanged top portion of the male piece and the proximal end of the female piece, between the center shaft and the column past the distal end of the female pice, through the capturing feature, and on a second side generally opposite the first side between the center shaft and the column and between the flanged top portion of the male piece and the proximal end of the female piece.

40. The securing device of claim 38 wherein the ledge has a diameter greater than a diameter of the cylindrical hollow opening and smaller than a diameter of the top portion.

41. The securing device of claim 39 further comprising a enlargement at the distal end of the hook-like capturing feature with a diameter greater than the diameter of the cylindrical hollow opening and wherein the female piece being pivotable relative to the male piece with the enlargement engaged with the cylindrical hollow opening and the ledge in a non-contacting relationship with the cylindrical hollow opening.

* * * * *